United States Patent [19]

Takasugi et al.

[11] Patent Number: 4,822,805
[45] Date of Patent: Apr. 18, 1989

[54] PYRIDYL-IMIDAZOLE COMPOUNDS WHICH HAVE USEFUL PHARMACEUTICAL ACTIVITY

[75] Inventors: Hisashi Takasugi, Osaka; Kiyotaka Ito, Ikeda; Shigetaka Nishino, Suita; Akito Tanaka, Toyonaka; Takao Takaya, Kawanishi, all of Japan

[73] Assignee: Fujisawa Pharmaceutical Co., Ltd., Osaka, Japan

[21] Appl. No.: 84,862

[22] Filed: Aug. 13, 1987

[30] Foreign Application Priority Data

Aug. 15, 1986 [GB] United Kingdom ............... 8619971
Jul. 7, 1987 [GB] United Kingdom ............... 8715932

[51] Int. Cl.$^4$ .................... A61K 31/44; C07D 401/04
[52] U.S. Cl. ................................... 514/341; 546/278
[58] Field of Search ......................... 546/278; 514/341

[56] References Cited

U.S. PATENT DOCUMENTS 3,707,475 12/1972 Lombardino ............ 548/336
3,929,807 12/1975 Fitzi .................... 546/278
4,440,774  4/1984 Baldwin ................. 548/336

Primary Examiner—Mary C. Lee
Assistant Examiner—Zinna Northington
Attorney, Agent, or Firm—Oblon, Fisher, Spivak, McClelland & Maier

[57] ABSTRACT

A compound of the formula:

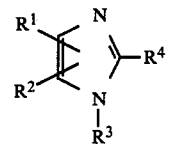

wherein
$R^1$ is pyridyl,
$R^2$ is hydrogen, lower alkyl or hydroxy (lower) alkyl,
$R^3$ is hydrogen, hydroxy or lower alkyl, and
$R^4$ is aryl optionally substituted with substituent(s) selected from the group consisting of lower alkylthio, lower alkylsulfinyl, lower alkylsulfonyl, nitro, amino, substituted amino, hydroxy, lower alkoxy, lower alkynyloxy, substituted or unsubstituted ar(lower)alkoxy, halogen, halo(lower)alkyl, carboxy and esterified carboxy, and a pharmaceutically acceptable salt thereof, processes for the preparation thereof and pharmaceutical composition comprising the same.

9 Claims, No Drawings

PYRIDYL-IMIDAZOLE COMPOUNDS WHICH HAVE USEFUL PHARMACEUTICAL ACTIVITY

This invention relates to new imidazole compounds and pharmaceutically acceptable salts thereof.

More particularly, this invention relates to new imidazole compounds and pharmaceutically acceptable salts thereof which have pharmacological activities, processes for the preparation thereof, a pharmaceutical composition comprising the same and method for the therapeutic treatment thereby.

One object of this invention is to provide the new and useful imidazole compounds and pharmaceutically acceptable salts thereof which possess cardiotonic activity and the capability of reducing heat rate; anti-platelet activity; and/or anti-inflammatory activity.

Another object of this invention is to provide processes for the preparation of the imidazole compounds and salts thereof.

A further object of this invention is to provide a pharmaceutical composition comprising, as active ingredients, said imidazole compounds or pharmaceutically acceptable salts thereof.

Still further object of this invention is to provide a method for therapeutic treatment of heart disease, thrombosis and inflammation of human beings or animals by administering said imidazole compounds or pharmaceutically acceptable salts thereof.

Some imidazole compounds having substituted or unsubstituted phenyl at 2-position of the imidazole ring have been known as described in U.S. Pat. Nos. 3,707,475, 4,440,774, etc..

The object imidazole compounds of this invention are novel and can be represented by the following general formula [I]:

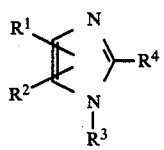

wherein
$R^1$ is pyridyl,
$R^2$ is hydrogen, lower alkyl or hydroxy(lower)alkyl,
$R^3$ is hydrogen, hydroxy or lower alkyl, and
$R^4$ is aryl optionally substituted with substituent(s) selected from the group consisting of lower alkylthio, lower alkylsulfinyl, lower alkylsulfonyl, nitro, amino, substituted amino, hydroxy, lower alkoxy, lower alkynyloxy, substituted or unsubstituted ar(lower)alkoxy, halogen, halo(lower)alkyl, carboxy and esterified carboxy.

The ojbect compound [I] or its salt can be prepared by processes as illustrated in the following reaction schemes.

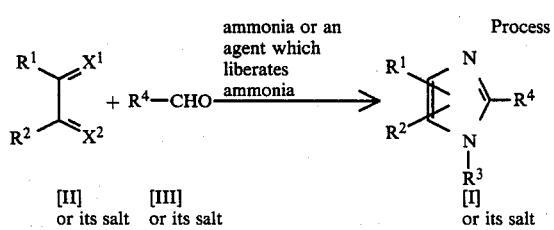

[II]   [III]
or its salt   or its salt

[I]
or its salt

-continued

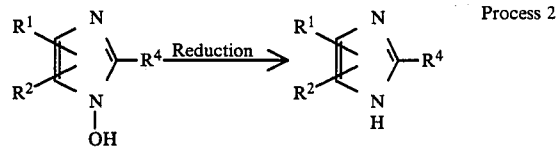

[Ia]   [Ib]
or its salt   or its salt

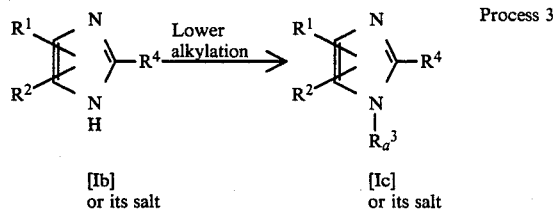

[Ib]   [Ic]
or its salt   or its salt

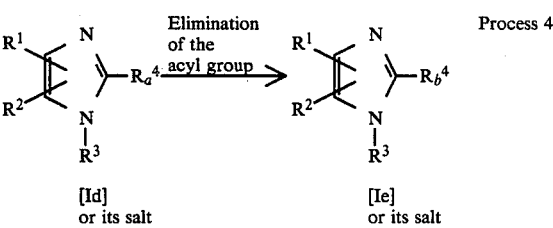

[Id]   [Ie]
or its salt   or its salt

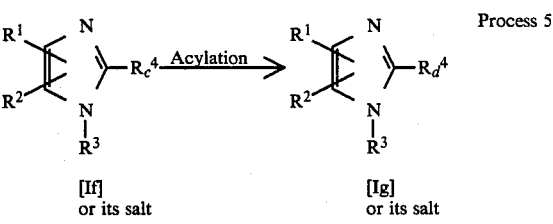

[If]   [Ig]
or its salt   or its salt

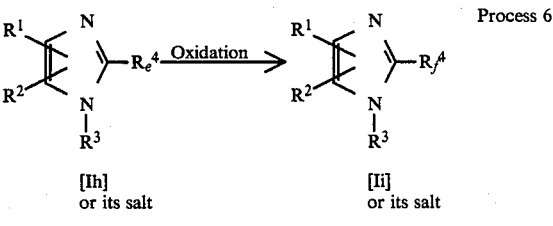

[Ih]   [Ii]
or its salt   or its salt

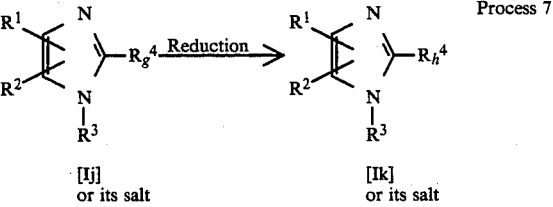

[Ij]   [Ik]
or its salt   or its salt

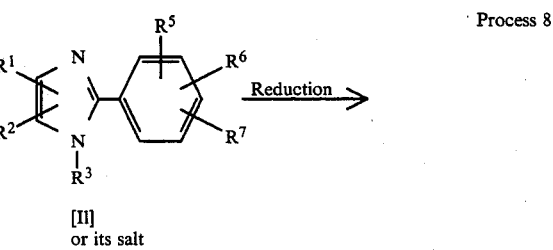

[II]
or its salt

-continued $$\text{[Im] or its salt}$$

Process 9

$$\text{[In] or its salt} \xrightarrow{\text{Halogenation}}$$

$$\text{[Io] or its salt}$$

Process 10

$$\text{[Ip] or its salt} \xrightarrow{\text{Reduction}} \text{[Iq] or its salt}$$

wherein
- $R_a{}^3$ is lower alkyl,
- $R_a{}^4$ is aryl substituted with acylamino and lower alkoxy, with acylamino, lower alkoxy and halogen, or with N-acyl-N-lower alkylamino, lower alkoxy and halogen,
- $R_b{}^4$ is aryl substituted with amino and lower alkoxy, with amino, lower alkoxy and halogen, or with lower alkylamino, lower alkoxy and halogen,
- $R_c{}^4$ is aryl substituted with amino, with amino and lower alkyl, with amino and lower alkoxy, with amino and halogen, with amino, lower alkoxy and nitro, or with amino, lower alkoxy and halogen,
- $R_d{}^4$ is aryl substituted with acylamino, with acylamino and lower alkyl, with acylamino and lower alkoxy, with acylamino and halogen, with acylamino, lower alkoxy and nitro, or with acylamino, lower alkoxy and halogen,
- $R_e{}^4$ is aryl substituted with lower alkylthio and lower alkoxy,
- $R_f{}^4$ is aryl substituted with lower alkylsulfinyl and lower alkoxy, or with lower alkylsulfonyl and lower alkoxy,
- $R_g{}^4$ is aryl substituted with nitro, with nitro and lower alkoxy, or with nitro, lower alkoxy and halogen,
- $R_h{}^4$ is aryl substituted with amino, with amino and lower alkoxy, or with amino, lower alkoxy and halogen,
- $R_i{}^4$ is aryl substituted with ar(lower)alkoxy and lower alkoxy,
- $R_j{}^4$ is aryl substituted with hydroxy and lower alkoxy,
- $R^5$ is halogen,
- $R^6$ and $R^7$ are each lower alkoxy or substituted amino,
- $R^8$ and $R^9$ are each lower alkoxy,
- one of $X^1$ and $X^2$ is O and the other is a group of the formula: $=N-R^3$, in which $R^3$ is as defined above, and
- $R^1$, $R^2$, $R^3$ and $R^4$ are each as defined above.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

Suitable "lower alkyl" and lower alkyl moiety in the term "hydroxy(lower)alkyl" may be a straight or branched one such as methyl, ethyl, propyl, isopropyl, butyl, isobutyl, tert-butyl, pentyl, hexyl or the like, in which the preferable one is $C_1$–$C_4$ alkyl and the most preferable one is methyl or ethyl.

Suitable "aryl" may be phenyl, naphthyl, lower alkyl substituted phenyl [e.g. tolyl, mesityl, cumenyl, etc.] or the like, in which the preferable one is phenyl or tolyl.

The aryl group for $R^4$ may be substituted with lower alkylthio [e.g. methylthio, ethylthio, propylthio, ispropylthio, butylthio, isobutylthio, tert-butylthio, pentylthio, hexylthio, etc.], lower alkylsulfinyl [e.g. methylsulfinyl, ethylsulfinyl, propylsulfinyl, isopropylsulfinyl, butylsulfinyl, isobutylsulfinyl, tert-butylsulfinyl, pentylsulfinyl, hexylsulfinyl, etc.], lower alkylsulfonyl [e.g. methylsulfonyl, ethylsulfonyl, propylsulfonyl, isopropylsulfonyl, butylsulfonyl, isobutylsulfonyl, tert-butylsulfonyl, pentylsulfonyl, hexylsulfonyl, etc.], nitro, amino, substituted amino such as mono- or di(lower)alkylamino [e.g. methylamino, ethylamino, propylamino, dimethylamino, diethylamino, methylethylamino, etc.], acylamino [e.g. lower alkanoylamino (e.g. formylamino, acetylamino, propionylamino, hexanoylamino, pivaloylamino, etc.), substituted or unsubstituted aroylamino (e.g. benzoylamino, 3-nitrobenzoylamino, 4-chlorobenzoylamino, etc.), lower alkoxycarbonylamino (e.g. methoxycarbonylamino, ethoxycarbonylamino, tert-butoxycarbonylamino, tert-pentyloxycarbonylamino, hexyloxycarbonylamino, etc.), ar(lower)alkoxycarbonylamino (e.g. benzyloxycarbonylamino, etc.), lower alkanesulfonylamino (e.g. mesylamino, ethanesulfonylamino, etc.), arenesulfonylamino (e.g. benzenesulfonylamino, tosylamino, etc.), ureido, thioureido, lower alkylureido (e.g. methylureido, ethylureido, propylureido, isopropylureido, etc.), lower alkylthioureido (e.g. methylthioureido, ethylthioureido, propylthioureido, isopropylthioureido, etc.), aroylthioureido (e.g. benzoylthioureido, etc.), etc.], N-acyl-N-lower alkylamino [e.g. N-lower alkanoyl-N-lower alkylamino (e.g. N-acetyl-N-methylamino, etc.), etc.] or the like, hydroxy, lower alkoxy [e.g. methoxy, ethoxy, propoxy, isopropoxy, butoxy, isobutoxy, tert-butoxy, pentyloxy, hexyloxy, etc.], lower alkynyloxy [e.g. ethynyloxy, propynyloxy, butynyloxy, etc.], substituted or unsubstituted ar(lower)alkoxy [e.g. benzyloxy, phenethyloxy, benzyhydryloxy, 4-chlorobenzyloxy, etc.], halogen [e.g. fluorine, chlorine, bromine and iodine], halo(lower)alkyl [e.g. chloromethyl, chloroethyl, trifluoromethyl, etc.], carboxy or esterified carboxy [e.g. lower alkoxycarbonyl (e.g. methoxycarbonyl, ethoxycarbonyl, tert-butoxycarbonyl, tert-pentyloxycarbonyl, hexyloxycarbonyl, etc.), etc.], wherein the number of the substituent(s) is 1 to 3 and plural substituents may be the same or different.

Suitable substituents of aryl for $R_a^4$ to $R_f^4$ can be referred to the ones as exemplified for the substituents of aryl for $R^4$.

Suitable "halogen" for $R^5$, "lower alkoxy" and "substituted amino" for $R^6$ and $R^7$ and "lower alkoxy" for $R^8$ and $R^9$ can be referred to the ones as exemplified for the substituents of aryl for $R^4$.

Suitable pharmaceutically acceptable salts of the object compound [I] are conventional non-toxic salts and include an organic acid addition salt [e.g. formate, acetate, trifluoroacetate, maleate, tartrate, methanesulfonate, benzenesulfonate, toluenesulfonate, etc.], an inorganic acid addition salt [e.g. hydrochloride, hydrobromide, sulfate, phosphate, etc.], a salt with an acidic amino acid [e.g. aspartic acid salt, glutamic acid salt, etc.], and the like.

With respect to the salt of the compounds [Ia] to [Iq] in the Processes 1 to 10, it is to be noted that these compounds are included within the scope of the compound [I], and accordingly the suitable examples of the salts of these compounds are to be referred to those as exemplified for the object compound [I].

The processes for preparing the object compounds [I] of the present invention are explained in detail in the following.

PROCESS 1

The object compound [I] or its salt can be prepared by reacting a compound [II] or its salt with a compound [III] or its salt in the presence of ammonia or an agent which liberates ammonia.

Suitable salts of the compound [II] may be the same as those exemplified for the compound [I] and further a base salt such as an alkali metal salt [e.g. lithium salt, sodium salt, potassium salt, etc.] or the like.

Suitable salts of the compound [III] may be the same as those exemplified for the compound [I].

This reaction is usually carried out in a conventional solvent such as water, alcohol [e.g. methanol, ethanol, propanol, etc.], acetic acid, dioxane, tetrahydrofuran, methylene chloride, chloroform, acetonitrile, N,N-dimethylformamide, dimethyl sulfoxide or any other organic solvent which does not adversely influence the reaction, or a mixture thereof.

Suitable agents which liberates ammonia may be ammonium lower alkanoate [e.g. ammonium formate, ammonium acetate, ammonium propionate, ammonium butyrate, etc.], ammonium carbonate, ammonium hydrogencarbonate, ammonium carbamate or the like.

The reaction temperature is not critical, and the reaction is usually carried out under cooling, at ambient temperature or under warming or heating.

PROCESS 2

The object compound [Ib] or its salt can be prepared by reducing a compound [Ia] or its salt.

The reduction can be carried out in a conventional manner, namely, chemical reduction or catalytic reduction.

Suitable reducing agents to be used in chemical reduction are a metal hydride compound such as aluminum hydride compound [e.g. lithium aluminum hydride, sodium aluminum hydride, aluminum hydride, lithium trimethoxyaluminum hydride, lithium tri-t-butoxyaluminum hydride, etc.], borohydride compound [e.g. sodium borohydride, lithium borohydride, sodium cyanoborohydride, tetramethylammonium borohydride, etc.], borane, diborane, aluminum halide [e.g. aluminum chloride, etc.], phosphorus trihalide [e.g. phosphorus trichloride, phosphorus tribromide, etc.], tri(lower)alkyl phosphite [e.g. triethyl phosphite, etc.], ferrous oxalate, a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.] or the like.

Suitable catalysts to be used in catalytic reduction are conventional ones such as platinum catalyst [e.g. platinum plate, spongy platinum, platinum black, colloidal platinum, platinum oxide, platinum wire, etc.], palladium catalyst [e.g. spongy palladium, palladium black, palladium oxide, palladium on carbon, colloidal palladium, palladium on barium sulfate, palladium on barium carbonate, etc.], nickel catalyst [e.g. reduced nickel, nickel oxide, Raney nickel, etc.], cobalt catalyst [e.g. reduced cobalt, Raney cobalt, etc.], iron catalyst [e.g. reduced iron, Raney iron, etc.], copper catalyst [e.g. reduced copper, Ullman copper, etc.] or the like.

The reaction of this process is usually carried out in a solvent such as water, alcohol [e.g. methanol, ethanol, propanol, etc.], acetic acid, diethyl ether, dioxane, tetrahydrofuran, methylene chloride, chloroform, N,N-dimethylformamide, dimethylsulfoxide, or any other organic solvent which does not adversely influence the reaction, or a mixture thereof.

The reaction is preferably carried out under somewhat milder conditions such as under cooling to warming.

In this reaction condition, hydroxy(lower)alkyl for $R^2$ may be obtained from the corresponding lower alkyl, and thus obtained product is also included within the scope of this process.

PROCESS 3

The object compound [Ic] or its salt can be prepared by subjecting a compound [Ib] or its salt to lower alkylation reaction.

Suitable lower alkylating agents to be used in this reaction may be lower alkyl halide [e.g. methyl iodide, ethyl iodide, propyl iodide, butyl iodide, butyl chloride, pentyl chloride, etc.], 2-lower alkylthio-2-imidazoline [e.g. 2-methylthio-2-imidazoline, etc.], lower alkyl sulfonate [e.g. methyl benzenesulfonate, ethyl mesylate, etc.], di(lower)alkyl sulfate [e.g. dimethyl sulfate, diethyl sulfate, etc.] or the like.

This reaction is usually carried out in the presence of a base such as an alkali metal [e.g. sodium, potassium, etc.], an alkaline earth metal [e.g. magnesium, calcium, etc. ], the hydride or hydroxide thereof, alkali metal alkoxide [e.g. sodium methoxide, sodium ethoxide, potassium tert-butoxide, etc.], trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like.

This reaction is usually carried out in a conventional solvent such as water, alcohol [e.g. methanol, ethanol, propanol, etc.], tetrahydrofuran, dioxane, ethyl acetate, methylene chloride, N,N-dimethylformamide, dimethyl sulfoxide, diethyl ether or any other organic solvent which does not adversely influence the reaction. And in case that the above-mentioned lower alkylating agent is in liquid, it can be also used as a solvent.

The reaction temperature is not critical, and the reaction is usually carried out under cooling, at ambient temperature or under warming or heating.

PROCESS 4

The object compound [Ie] or its salt can be prepared by subjecting a compound [Id] or its salt to elimination reaction of the acyl group.

This reaction is carried out in accordance with a conventional method such as hydrolysis, reduction or the like.

The hydrolysis is preferably carried out in the presence of a base or an acid including Lewis acid. Suitable base may be an alkali metal [e.g. sodium, potassium, etc.], an alkaline earth metal [e.g. magnesium, calcium, etc.], the hydroxide or carbonate or bicarbonate thereof, alkali metal alkanoate [e.g. sodium acetate, etc.], or the like. Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, etc.]. The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof of any other solvent which does not adversely influence the reaction. A liquid base or acid can be also used as the solvent. The reaction temperature is not critical and the reaction is usually carried out under cooling to heating.

The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction can be referred to the ones as exemplified in Process 2.

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof. The reaction temperature is not critical and the reaction is usually carried out under cooling to warming.

PROCESS 5

The object compound [Ig] or its salt can be prepared by reacting a compound [If] or its salt with an acylating agent.

Suitable acylating agents are the corresponding acid compounds, which are represented by the formula: $R^{10}$—OH wherein $R^{10}$ is acyl, and its reactive derivative, and the corresponding isocyanate or isothiocyanate compounds.

As suitable said reactive derivatives, there may be mentioned acid halides, acid anhydrides, active amides and active esters. Suitable examples are acid halides such as acid chloride and acid bromide, mixed acid anhydrides with various acids [e.g. substituted phosphoric acid such as dialkyl phosphoric acid, sulfuric acid, aliphatic carboxylic acid, aromatic carboxylic acid, etc.], symmetric acid anhydrides, active amides with various imidazoles, and active esters such as cyanomethyl ester, methoxymethyl ester, p-nitrophenyl ester, 2,4-dinitrophenyl ester, pentachlorophenyl ester, phenylazophenyl ester, carboxymethylthio ester and N-hydroxysuccinimide ester. The kind of such reactive derivatives can be selected depending on the kind of acyl group to be introduced.

The reaction is usually carried out in a conventional solvent, such as alcohol [e.g. methanol, ethanol, etc.], methylene chloride, chloroform, benzene, toluene, pyridine, diethyl ether, dioxane, tetrahydrofuran acetone, acetonitrile, ethyl acetate, acetic acid, N,N-dimethylformamide or any other organic solvent which does not adversely affect the reaction. In case that the acylating agent is liquid, it can also be used as a solvent. In case that the carboxylic acid compounds are used as acylating agent in the free acid form or salt form, it is preferable to carry out the reaction in the presence of a conventional condensing agent such as N,N'-dicyclohexylcarbodiimide or the like.

The reaction temperature is not critical and the reaction can be carried out under cooling, at ambient temperature, or under heating.

This reaction is preferably carried out in the presence of an inorganic base, for example an alkali metal hydroxide such as sodium hydroxide or potassium hydroxide, or an alkali metal carbonate or hydrogen carbonate such as sodium carbonate, potassium carbonate, sodium hydrogen carbonate or potassium hydrogen carbonate, or in the presence of an organic base, for example a tertiary amine such as triethylamine, pyridine or N,N-dimethylaniline.

PROCESS 6

The compound [Ii] or its salt can be prepared by oxidizing a compound [Ih] or its salt.

The present oxidation reaction can be carried out by a conventional method which is applied for the transformation of —S— into —SO— or —SO$_2$—, for example by using an oxidizing agent such as m-chloroperbenzoic acid, perbenzoic acid, peracetic acid, ozone, hydrogen peroxide, periodic acid, potassium permanganate or the like.

The present reaction is usually carried out in a solvent such as water, acetone, dioxane, acetonitrile, acetic acid, chloroform, ethylene chloride, ethyl acetate or any other solvents which do not adversely affect the reaction.

The reaction temperature is not critical, and the reaction is preferably carried out under cooling or at ambient temperature.

PROCESS 7

The object compound [Ik] or its salt can be prepared by reducing a compound [Ij] or its salt.

The reduction can be carried out in a conventional manner, namely, chemical reduction or catalytic reduction.

Suitable reducing agents to be used in chemical reduction may be a combination of metal [e.g. tin, zinc, iron, etc.] and ammonium chloride or a base [e.g. ammonia, sodium hydroxide, etc.], a combination of the above-mentioned metal or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.], alkali metal borohydride [e.g. lithium borohydride, sodium borohydride, potassium borohydride etc.], alkali metal cyanoborohydride [e.g. sodium cyanoborohydride, etc.] or alkali metal aluminum hydride [e.g. lithium aluminum hydride, etc.] or the like.

Suitable catalysts to be used in catalytic reduction can be referred to the ones as exemplified in Process 2.

The reaction of this process is usually carried out in a solvent such as water, alcohol [e.g. methanol, ethanol, propanol, etc.], acetic acid diethyl ether, dioxane, tetrahydrofuran, etc. or a mixture thereof.

The reaction is usually carried out under cooling to warming or heating.

PROCESS 8

The object compound [Im] or its salt can be prepared by reducing a compound [Il] or its salt.

This reaction can be carried out in substantially the same manner as that of Process 7, and therefore the reaction mode and reaction conditions of this reaction can be referred to those as explained in Process 7.

PROCESS 9

The object compound [Io] or its salt can be prepared by halogenating a compound [In] or its salt.

The halogenation is carried out in the presence of a halogenating agent.

Suitable halogenating agents of this reaction may be halogen [e.g. chlorine, bromine, iodine, etc.], sulfuryl halide [e.g. sulfuryl chloride, sulfuryl bromide, etc.], N-halosuccinimide [e.g. N-chlorosuccinimide, N-bromosuccinimide, etc.], pyridinium hydrohalide perhalide [e.g. pyridinium hydrobromide perbromide, pyridinium hydrochloride perchloride, etc.], quarternary ammonium perhalide [e.g., phenyltrimethylammonium perbromide, etc.], $\omega$-trihaloacetophenone [e.g. $\omega$-tribromoacetophenone, etc.], selenium oxychloride and the like. These halogenating agents may be selected according to the kind of the starting compound [In] to be used.

This reaction is usually carried out in a conventional solvent such as chloroform, methylene chloride, carbon tetrachloride, N,N-dimethylformamide, acetic acid, a mixture of hydrogen halide [e.g. hydrogen bromide, hydrogen chloride, etc.] and acetic acid or the like.

The reaction temperature is not critical, and the reaction is usually carried out at ambient temperature or under warming or heating.

PROCESS 10

The object compound [Ig] or its salt can be prepared by reducing a compound [Ip] or its salt.

This reaction can be carried out by a catalytic reduction method.

This catalytic reduction can be carried out in substantially the same manner as that of Process 7, and therefore the reaction mode and reaction conditions of this reaction can be referred to those as explained in Process 7.

The compounds obtained by the above processes are isolated and purified by a conventional method such as pulverization, recrystallization, column chromatography, reprecipitation or the like.

The new imidazole compounds [I] and pharmaceutically acceptable salts thereof possess cardiotonic activity and the capability of reducing heart rate; anti-platelet activity; and/or anti-inflammatory activity, and are useful for a therapeutic treatment of heart diseases such as cardiac insufficiency, thrombosis, and inflammation.

For therapeutic purpose, the compound [I] and a pharmaceutically acceptable salt thereof of the present invention can be used in the form of pharmaceutical preparation containing one of said compounds, as an active ingredient, in admixture with a pharmaceutically acceptable carrier such as an organic or inorganic solid or liquid excipient suitable for oral, parenteral or external administration. The pharmaceutical preparations may be capsules, tablets, dragees, granules, solution, suspension, emulsion, or the like. If desired, there may be included in these preparations, auxiliary substances, stabilizing agents, wetting or emulsifying agents, buffers and other commonly used additives.

While the dosage of the compound [I] will vary depending upon the age and condition of the patient, an average single dose of about 0.1 mg, 1 mg, 10 mg, 50 mg, 100 mg, 250 mg, 500 mg and 1000 mg of the compound [I] may be effective for treating the above-mentioned diseases. In general, amounts between 0.1 mg/body and about 1,000 mg/body may be administered per day.

In order to illustrate the usefulness of the object compound [I], the pharmacological test data of some representative compounds of the compound [I] are shown in the following.

TEST COMPOUNDS 2-(2,4-Dimethoxyphenyl)-5-methyl-4-(3-pyridyl)imidazole (hereinafter referred to as Compound a)

2-(2,4-Dimethoxyphenyl)-4-ethyl-5-(3-pyridyl)imidazole (hereinafter referred to as Compound b)

2-(2-Methoxy-4-methylthiophenyl)-5-methyl-4-(3-pyridyl)imidazole (hereinafter referred to as Compound c)

2-(3,4-Dimethoxyphenyl)-5-ethyl-4-(2-pyridyl)imidazole (hereinafter referred to as Compound d)

2-(2,4-Dimethoxyphenyl)-5-methyl-4-(4-pyridyl)imidazole (hereinafter referred to as Compound e)

2-(2,4-Dimethoxyphenyl)-5-ethyl-4-(4-pyridyl)imidazole (hereinafter referred to as Compound f)

2-(4-Acetamido-5-chloro-2-methoxyphenyl)-5-methyl-4-(3-pyridyl)imidazole (hereinafter referred to as Compound g)

2-(2-Methoxyphenyl)-5-methyl-4-(3-pyridyl)imidazole (hereinafter referred to as Compound h)

2-(2-Fluorophenyl)-4-methyl-5-(3-pyridyl)imidazole (hereinafter referred to as Compound i)

2-(2-Acetamidophenyl)-4-methyl-5-(3-pyridyl)imidazole (hereinafter referred to as Compound j)

2-(4-Chloro-2-methoxyphenyl)-5-methyl-4-(3-pyridyl)imidazole (hereinafter referred to as Compound k).

CARDIOTONIC ACTIVITY

Test 1

Test Method

Mongrel dogs of either sex were anesthetized with sodium pentobarbital, 35 mg/kg, i.p.. The animals were allowed to breathe spontaneously. The left carotid artery was isolated and a catheter (USCI, #8F) filled with heparinized saline was inserted and advanced into the left ventricle. The catheter was connected to a pressure transducer (Nihonkohden, MPU-0.5A) to measure the left ventricular pressure, from which dp/dt max was derived by analog computing. The measure the systemic blood pressure the left femoral artery was cannulated. The blood pressure pulse was used to trigger a heart rate meter. Another catheter was positioned in the vena cave through right femoral vein for injection of drugs. Systemic blood pressure, left ventricular pressure, dp/dt max and heart rate was recorded simultaneously on a polygram (Nihonkohden, RJG-4008).

Test compound was dissolved in distilled water (0.2 ml/kg) or dimethyl sulfoxide (0.04 ml/kg) and injected into the femoral vein. The parameters after dosing were compared with those during the predosing period.

Test results were represented in terms of percentage of dp/dt max changes (dp/dt M.C.) calculated by following formula.

$$dp/dt\ M.C.\ (\%) = \left(\frac{dp/dt\ \text{max after dosing}}{dp/dt\ \text{max before dosing}} - 1\right) \times 100$$

Test Results

| Compound | Dose (mg/kg) | dp/dt M.C. (%) |
|---|---|---|
| a | 1.0 | 82 |
| b | 1.0 | 133 |
| c | 1.0 | 167 |

Test 2

Test Method

Male Hartley strain guinea-pigs, weighing 530–600 g, were killed by bleeding and the heart was removed. An atrial strip was removed and suspended in an organ bath containing 50 ml of Tyrode's solution maintained at 30° C. and aerated with a gas mixture of 95% $O_2$–5% $CO_2$. The atrium was connected to a strain gauge under an initial tension of 0.4–0.6 g. After constant motility had been obtained the drug was added to the bath solution and the effect on contractile force and heart rate was observed for 30 min. The effect was expressed as percentage values before and after dosing.

Test Results

| Compound | Concentration (g/ml) | Force (%) | Heart Rate (%) |
|---|---|---|---|
| a | $1 \times 10^{-5}$ | 45.0 | −21.2 |
| d | $1 \times 10^{-5}$ | 51.6 | −14.1 |
| e | $1 \times 10^{-5}$ | 58.0 | −26.8 |
| f | $1 \times 10^{-5}$ | 61.1 | −30.7 |

ANTI-PLATELET ACTIVITY

Test 3

Test Method

Male Sprague-Dawley rats weighing about 250 g were used after overnight fasting. One hour after oral administration of test compound or vehicle of test compound (control), blood was collected into a tube containing 0.1 vol. of 3.8% sodium citrate. To the 0.45 ml of blood, 0.05 ml of collagen (final concentration 5.0 μg/ml) was added and then incubated for 5 min. at 37° C. under shaking. The reaction was terminated by addition of 1 ml of 10 mM phosphate buffered saline (pH 7.4) containing 11.5 mM EDTA and 1% formalin. The reaction mixture was centrifuged at 70 xg for 5 min. and platelet count of upper phase was measured by Technicon Auto Analizer.

Platelet aggregation was calculated according to the following formula:

$$\text{Platelet aggregation (\%)} = \frac{A - B}{A} \times 100$$

A: Platelet count after addition of vehicle of collagen
B: Platelet count after addition of collagen.

Inhibition of the test compound was calculated according to the following formula.

$$\text{Inhibition (\%)} = \frac{C - D}{C} \times 100$$

C: Platelet aggregation (%) of control
D: Platelet aggregation (%) of Test compound.

Test Results

| Compound | Dose (mg/kg) | Inhibition (%) |
|---|---|---|
| g | 32 | 87.6 |
| i | 32 | 100 |
| j | 32 | 91.3 |

Test 4

Test Method

The blood was collected from the carotid artery of rabbits into plastic vessels containing 0.1 volume of 3.8% sodium citrate. Platelet rich plasma (PRP) was prepared by centrifugation at 150 g for 15 minutes. Platelet aggregation was investigated by using the turbidimetric method with an aggregometer (NKK HEMATRACER 1). To the 225 μl of PRP, 25 μl of test compound solution was added, and then stirred at 1000 rpm for 2 minutes at 37° C. To the solution 5 μl of 9,11-azo $PGH_2$ (final 1.0 μM) was added as an aggregating inducer.

Test Results

| Compound | $IC_{50}$ (g/ml) |
|---|---|
| i | $1.1 \times 10^{-7}$ |
| j | $3.9 \times 10^{-7}$ |
| k | $1.6 \times 10^{-7}$ |

ANTI-INFLAMMATORY ACTIVITY

Test 5

Test Method

Male Sprague-Dawley rats weighing about 180 g were used in groups of five. Paw edema was induced by subplantar injection of 1% carrageenin (0.1 ml/rat) into the right hind paw in carrageenin foot edema. The test compound was suspended in methylcellulose and administered orally 60 minutes before halogogen. Paw volume was measured with plethysmometer (Ugo Basil Co., Ltd.) by water displacement immersing the paw to the lateral malleolus. The difference of paw volume before and 3 hours after the phlogogen was designated as edema volume.

The data was analyzed statistically by student's t-test.

Test Results

| Compound | Dose (mg/kg) | Inhibition (%) |
|---|---|---|
| h | 32 | 62.7 |
| k | 32 | 72.3 |

The following Preparations and Examples are given for the purpose of illustrating the present invention in more detail.

PREPARATION 1

To a solution of isoamyl nitrite (2.6 ml) and sodium methoxide (28% in methanol, 3.4 ml) in methanol (40 ml) was added dropwise a solution of 4-propionylpyridine (2.0 g) in methanol (10 ml) under ice-cooling. The reaction mixture was stirred at ambient temperature for 3 hours, and then neutralized with 1N hydrochloric acid. After evaporation to remove methanol, the organic layer was extracted with ethyl acetate. The extract was washed with brine, dried over sodium sulfate, evaporated and triturated with diisopropyl ether to give 4-(2-hydroxyiminopropionyl)pyridine (0.95 g).

mp: 150°–151° C.

IR (Nujol): 1670, 1605 $cm^{-1}$.

NMR ($CDCl_3$, δ): 2.15 (3H, s), 7.65 and 8.60 (4H, AB type, J=7 Hz).

The following compounds (Preparations 2 to 4) were obtained according to a similar manner to that of Preparation 1.

PREPARATION 2

4-(2-Hydroxyiminobutyryl)pyridine.
mp: 146°–149° C.
IR (Nujol): 3250, 1680, 1590 $cm^{-1}$.

PREPARATION 3

1-Hydroxyimino-1-(3-pyridyl)-2-butanone.
mp: 172°–174° C.
IR (Nujol): 1690, 1600, 1585 $cm^{-1}$.
NMR (DMSO-$d_6$, δ): 1.10 (3H, t, J=7 Hz), 2.98 (2H, q, J=7 Hz), 7.45 (1H, dd, J=8 Hz, J=8 Hz), 7.70 (1H, ddd, J=8 Hz, J=2 Hz, J=2 Hz), 8.45–8.70 (2H, m).

PREPARATION 4

2-(2-Hydroxyiminobutyryl)pyridine.
mp: 134°–135° C.
IR (Nujol): 1670, 1580, 1490 $cm^{-1}$.
NMR ($CDCl_3$, δ): 1.16 (3H, t, J=7 Hz), 2.78 (2H, q, J=7 Hz), 7.2–7.5 (1H, m), 7.7–8.1 (1H, m), 7.90 (1H, d, J=2 Hz), 8.63 (1H, dd, J=5.5 Hz, 2 Hz).

EXAMPLE 1

To a suspension of 4-(2-hydroxyiminopropionyl)pyridine (2.0 g) in a mixture of dioxane (40 ml) and ethanol were added conc. ammonia water (58 ml) and 2,4-dimethoxybenzaldehyde (2.02 g), and the mixture was stirred at ambient temperature for 1 week. After evaporation, the mixture was triturated with chloroform to give 1-hydroxy-2-(2,4-dimethoxyphenyl)-5-methyl-4-(4-pyridyl)imidazole (3.01 g).

mp: 240°–241° C.

IR (Nujol): 1605 $cm^{-1}$.

NMR (DMSO-$d_6$, δ): 2.38 (3H, s), 3.77 (3H, s), 3.83 (3H, s), 6.5–6.9 (2H, m), 7.31 (1H, d, J=8 Hz), 7.67 (2H, d, J=6 Hz), 8.55 (2H, d, J=6 Hz).

EXAMPLE 2

To a suspension of 1-hydroxyimino-1-(3-pyridyl)acetone (1.5 g) in a mixture of dioxane (30 ml) and ethanol (8 ml) were added conc. ammonia water (40 ml) and 2-methoxybenzaldehyde (1.24 g), and the mixture was stirred at ambient temperature for 8 days. After evaporation, the mixture was triturated with chloroform to give 1-hydroxy-2-(2-methoxyphenyl)-4-methyl-5-(3-pyridyl)imidazole (1.65 g).

mp: 105°–120° C.

IR (Nujol): 1605 $cm^{-1}$.

NMR (DMSO-$d_6$, δ): 2.22 (3H, s), 3.73 (3H, s), 6.7–7.6 (5H, m), 7.92 (1H, ddd, J=2 Hz, 2 Hz, 8 Hz), 8.47 (1H, dd, J=2 Hz, 5 Hz), 8.72 (1H, d, J=2 Hz).

EXAMPLE 3

To a suspension of 1-hydroxyimino-1-(3-pyridyl)acetone (1.64 g) in a mixture of dioxane (30 ml), ethanol (10 ml), and water (5 ml) were added 3,4-dimethoxybenzaldehyde (1.66 g) and conc. ammonia water (0.69 ml). The solution was stirred at 60° C. for 2 hours. Additional ammonia water (0.7 ml) was added thereto, and the solution was stirred at 45° to 50° C. for 1 day. The mixture was evaporated, and the residue was dissolved in chloroform, and subjected to column chromatography on silicagel eluting with a mixture of chloroform and methanol. The fractions were collected and evaporated, and the residue was triturated with diisopropyl ether to give 1-hydroxy-2-(3,4-dimethoxyphenyl)-4-methyl-5-(3-pyridyl)imidazole (1.20 g).

mp: 131°–135° C.

IR (Nujol): 1505, 1260, 1230 $cm^{-1}$.

NMR (DMSO-$d_6$, δ): 2.26 (3H, s), 3.80 (3H, s), 3.83 (3H, s), 7.04 (1H, d, J=9 Hz), 7.3–8.1 (4H, m), 8.56 (1H, dd, J=2 Hz, 5 Hz), 8.75 (1H, d, J=2 Hz).

EXAMPLE 4

To a suspension of 1-hydroxyimino-1-(3-pyridyl)acetone (3.3 g) in a mixture of dioxane (80 ml), ethanol (20 ml) and conc. ammonia water (40 ml) was added 4-acetamido-5-chloro-2-methoxybenzaldehyde (4.54 g) and the resultant mixture was stirred at ambient temperature for 3 days. The reaction mixture was evaporated in vacuo and the residue was dissolved in a mixture of ethyl acetate and 5% hydrochloric acid. The separated aqueous layer was adjusted to pH8.0 with 20% potassium carbonate under stirring and the precipitate was collected by filtration and dried to give 1-hydroxy-2-(4-acetamido-5-chloro-2-methoxyphenyl)-4-methyl-5-(3-pyridyl)imidazole (3.1 g).

mp: 178°–180° C. (dec.)

IR (Nujol): 3450, 3150, 1660, 1600, 1570, 1530, 1505 $cm^{-1}$.

NMR ($D_2O$-DCl, δ): 2.35 (3H, s), 2.60 (3H, s), 4.00 (3H, s), 7.83 (1H, s), 8.07 (1H, s), 8.40 (1H, dd, J=6 Hz, 8 Hz), 8.95 (1H, dd, J=2 Hz, 8 Hz), 9.08 (1H, dd, J=2 Hz, 6 Hz), 9.25 (1H, d, J=2 Hz)

Mass (m/e): 372 ($M^+$).

EXAMPLE 5

To a suspension of 1-hydroxyimino-1-(3-pyridyl)acetone (1.0 g) in a mixture of dioxane (20 ml) and ethanol (6 ml), were added 2-methoxy-4-methylbenzaldehyde (1.01 g) and conc. ammonia water (15 ml). The solution was stirred at ambient temperature for 8 days. After evaporation, the residue was dissolved in chloroform, and chromatographed on silicagel eluting with a mixture of chloroform and methanol. The fractions were collected, evaporated, and triturated in diisopropyl ether to give 1-hydroxy-2-(2-methoxy-4-methylphenyl)-4-methyl-5-(3-pyridyl)imidazole (1.46 g).

mp: 75°–80° C.

IR (Nujol): 1615, 1580 cm$^{-1}$.

NMR (DMSO-d$_6$, δ): 2.24 (3H, s), 2.34 (3H, s), 3.75 (3H, s), 6.74 (1H, d, J=8 Hz), 6.88 (1H, s), 7.6–7.2 (2H, m), 7.87 (1H, ddd, J=8 Hz, J=2 Hz, J=2 Hz), 8.43 (1H, dd, J=5 Hz, J=2 Hz), 8.65 (1H, d, J=2 Hz), 11.35 (1H, br s).

Mass: (M/Z): 295 (M+).

The following compounds (Examples 6 to 119) were obtained according to a similar manner to that of Example 1, 2, 3, 4 or 5.

EXAMPLE 6

1-Hydroxy-2-(2,4-dimethoxyphenyl)-5-methyl-4-(2-pyridyl)imidazole mp: 141°–144° C. (dec.)

IR (Nujol): 1600, 1570, 1460, 1310, 1280 cm$^{-1}$.

NMR (CDCl$_3$, δ): 2.49 (3H, s), 3.73 (3H, s), 3.86 (3H, s), 6.3–6.6 (2H, m), 7.0–7.4 (1H, m), 7.6–7.8 (2H, m), 8.4–8.8 (2H, m).

Mass (m/e): 311 (M+).

EXAMPLE 7

1-Hydroxy-2-(2,4-dimethoxyphenyl)-5-ethyl-4-(4-pyridyl)imidazole mp: 206°–208° C. (dec.).

IR (Nujol): 1600, 1570, 1520, 1430 cm$^{-1}$.

NMR (DMSO-d$_6$, δ): 1.23 (3H, t, J=7 Hz), 2.86 (2H, q, J=7 Hz), 3.73 (3H, s), 3.83 (3H, s), 6.58 (1H, d, J=8 Hz), 6.70 (1H, s), 7.35 (1H, d, J=8 Hz), 7.65 (2H, dd, J=2 Hz, 5 Hz), 8.55 (2H, dd, J=2 Hz, 5 Hz).

EXAMPLE 8

1-Hydroxy-2-(3,4-dimethoxyphenyl)-5-methyl-4-(4-pyridyl)imidazole mp: 131°–136° C.

IR (Nujol): 1610, 1600 cm$^{-1}$.

NMR (DMSO-d$_6$, δ): 2.47 (3H, s), 3.80 (3H, s), 3.83 (3H, s), 7.05 (1H, d, J=9 Hz), 7.6–7.9 (4H, m), 8.23 (2H, br d, J=6 Hz).

EXAMPLE 9

1-Hydroxy-2-(3,4-dimethoxyphenyl)-5-methyl-4-(2-pyridyl)imidazole.

mp: 141°–144° C. (dec.).

IR (Nujol): 3200, 1603, 1595, 1560, 1500 cm$^{-1}$.

NMR (DMSO-d$_6$, δ): 2.62 (3H, s), 3.78 (3H, s), 3.81 (3H, s), 6.99 (1H, d, J=9 Hz), 7.0–7.2 (1H, m), 7.5–7.7 (2H, m), 7.75 (1H, dd, J=2 Hz, 8 Hz), 7.96 (1H, d, J=8 Hz), 8.4–8.6 (1H, m), 10.7 (1H, br s).

EXAMPLE 10

1-Hydroxy-2-(3,4-dimethoxyphenyl)-5-ethyl-4-(4-pyridyl)imidazole

IR (Nujol): 3470, 3200, 1600, 1520, 1430 cm$^{-1}$.

NMR (DMSO-d$_6$, δ): 1.18 (3H, t, J=7 Hz), 2.82 (2H, q, J=7 Hz), 3.74 (6H, s), 6.90 (1H, d, J=9 Hz), 7.6–7.8 (3H, m), 7.76 (1H, s), 8.51 (2H, dd, J=6 Hz, 8 Hz).

EXAMPLE 11

1-Hydroxy-2-(3,4-dimethoxyphenyl)-5-ethyl-4-(2-pyridyl)imidazole.

mp: 92°–94° C.

IR (Nujol): 1590, 1510, 1490, 1270 cm$^{-1}$.

NMR (DMSO-d$_6$, δ): 1.24 (3H, t, J=8 Hz), 3.15 (2H, q, J=8 Hz), 3.80 (3H, s), 3.83 (3H, s), 7.01 (1H, d, J=9 Hz), 7.0–7.2 (1H, m), 7.5–7.7 (2H, m), 7.74 (1H, dd, J=2 Hz, 8 Hz), 7.98 (1H, d, J=8 Hz), 8.48 (1H, m), 11.6 (1H, br s).

Mass (m/e): 325 (M+).

EXAMPLE 12

1-Hydroxy-2-(3,4-dimethoxyphenyl)-4-(2-pyridyl)imidazole.

mp: 71°–73° C.

IR (Nujol): 1590, 1500, 1440 cm$^{-1}$.

NMR (CDCl$_3$, δ): 3.94 (3H, s), 3.95 (3H, s), 6.92 (1H, d, J=9 Hz), 7.0–7.4 (2H, m), 7.5–7.9 (3H, m), 7.66 (1H, s), 8.56 (1H, d, J=5 Hz).

Mass (m/e): 296 (M−1).

EXAMPLE 13

1-Hydroxy-5-methyl-2-phenyl-4-(3-pyridyl)imidazole.

mp: 75°–85° C.

IR (Nujol): 1600 cm$^{-1}$.

NMR (DMSO-d$_6$, δ): 2.43 (3H, s), 7.2–7.5 (4H, m), 7.8–8.1 (3H, m), 8.34 (1H, br d, J=4 Hz), 8.81 (1H, br s), 11.7 (1H, br s).

EXAMPLE 14

1-Hydroxy-2-(2,5-dimethoxyphenyl)-4-methyl-5-(3-pyridyl)imidazole mp: 115°–125° C.

IR (Nujol): 1590 cm$^{-1}$.

NMR (DMSO-d$_6$, δ): 2.19 (3H, s), 3.65 (6H, s), 6.8–7.2 (3H, m), 7.30 (1H, dd, J=5 Hz, 8 Hz), 7.84 (1H, ddd, J=8 Hz, 2 Hz, 2 Hz), 8.43 (1H, dd, J=2 Hz, 5 Hz), 8.66 (1H, d, J=7 Hz).

EXAMPLE 15

1-Hydroxy-2-(2,4-dimethoxyphenyl)-4-ethyl-5-(3-pyridyl)imidazole.

mp: 75°–80° C.

IR (Nujol): 1615, 1583 cm$^{-1}$.

NMR (DMSO-d$_6$, δ): 1.17 (3H, t, J=7 Hz), 2.40–2.55 (2H, m), 3.75 (3H, s), 3.80 (3H, s), 6.57 (1H, dd, J=8 Hz, 2 Hz), 6.66 (1H, s), 7.30–7.5 (1H, m), 7.67 (1H, dd, J=8 Hz, 4 Hz), 7.91 (1H, ddd, J=8 Hz, 2 Hz, 2 Hz), 8.50 (1H, dd, J=4 Hz, 2 Hz), 8.67 (1H, d, J=2 Hz).

EXAMPLE 16

1-Hydroxy-2-(3,4-dimethoxyphenyl)-4-ethyl-5-(3-pyridyl)imidazole.

mp: 75°–80° C.

IR (Nujol): 1608, 1587, 1512 cm$^{-1}$.

NMR (DMSO-d$_6$, δ): 1.17 (3H, t, J=7 Hz), 2.40–2.65 (2H, m), 3.75 (3H, s), 3.80 (3H, s), 7.00 (1H, d, J=8 Hz), 7.32–7.75 (3H, m), 7.86 (1H, ddd, J=8 Hz, 2 Hz, 2 Hz), 8.50 (1H, dd, J=4 Hz, 2 Hz), 8.63 (1H, d, J=2 Hz).

EXAMPLE 17

1-Hydroxy-2-(2,3-dimethoxyphenyl)-4-methyl-5-(3-pyridyl)imidazole.

mp: 110°–115° C.

IR (Nujol): 1580 cm$^{-1}$.

NMR (DMSO-d$_6$, δ): 2.27 (3H, s), 3.78 (3H, s), 3.86 (3H, s), 7.13 (3H, s), 7.48 (1H, dd, J=8 Hz, 4 Hz), 7.98 (1H, ddd, J=8 Hz, 2 Hz, 2 Hz), 8.52 (1H, dd, J=2 Hz, 4 Hz), 8.75 (1H, d, J=2 Hz).

EXAMPLE 18

1-Hydroxy-2-(3,4,5-trimethoxyphenyl)-4-methyl-5-(3-pyridyl)imidazole.
mp: 135°–138° C.
IR (Nujol): 1590 cm$^{-1}$.
NMR (DMSO-d$_6$, δ): 2.24 (3H, s), 3.73 (3H, s), 3.80 (6H, s), 7.40 (2H, s), 7.48 (1H, dd, J=8 Hz, 5 Hz), 7.95 (1H, ddd, J=8 Hz, 2 Hz, 2 Hz), 8.53 (1H, br d, J=5 Hz), 8.73 (1H, br s).

EXAMPLE 19

1-Hydroxy-2-(2,3,4-trimethoxyphenyl)-4-methyl-5-(3-pyridyl)imidazole.
mp: 90°–100° C.
IR (Nujol): 1600 cm$^{-1}$.
NMR (DMSO-d$_6$, δ): 2.26 (3H, s), 3.79 (6H, s), 3.86 (3H, s), 6.87 (1H, d, J=8 Hz), 7.26 (1H, d, J=8 Hz), 7.44 (1H, dd, J=8 Hz, 4 Hz), 7.92 (1H, ddd, J=2 Hz, 2 Hz, 8 Hz), 8.50 (1H, dd, J=2 Hz, 4 Hz), 8.73 (1H, d, J=2 Hz).

EXAMPLE 20

1-Hydroxy-2-(2-methoxy-4-nitrophenyl)-4-methyl-5-(3-pyridyl)imidazole
NMR (DMSO-d$_6$, δ): 2.31 (3H, s), 3.96 (3H, s), 7.45 (1H, dd, J=8 Hz, 4 Hz), 7.75–8.08 (4H, m), 8.48 (1H, d, J=4 Hz), 8.73 (1H, br s).

EXAMPLE 21

1-Hydroxy-2-(4-chloro-2-methoxyphenyl)-4-methyl-5-(3-pyridyl)imidazole.
mp: 130°–135° C.
IR (Nujol): 1600, 1575 cm$^{-1}$.
NMR (DMSO-d$_6$, δ): 2.19 (3H, s), 3.70 (3H, s), 6.83 (1H, dd, J=2 Hz, 8 Hz), 7.03 (1H, d, J=2 Hz), 7.22 (1H, d, J=8 Hz), 7.31 (1H, dd, J=8 Hz, 4 Hz), 7.82 (1H, ddd, J=8 Hz, 2 Hz, 2 Hz), 8.38 (1H, dd, J=2 Hz, 4 Hz), 8.61 (1H, d, J=2 Hz).

EXAMPLE 22

1-Hydroxy-2-(4-acetamido-2-methoxyphenyl)-4-methyl-5-(3-pyridyl)imidazole.
mp: 170°–175° C.
IR (Nujol): 1680, 1610 cm$^{-1}$.
NMR (DMSO-d$_6$, δ): 2.05 (3H, s), 2.23 (3H, s), 3.71 (3H, s), 7.6–7.0 (4H, m), 7.86 (1H, br d, J=8 Hz), 8.40 (1H, dd, J=4 Hz, 2 Hz), 8.64 (1H, br s), 9.96 (1H, br s), 11.05 (1H, br s).

EXAMPLE 23

1-Hydroxy-2-[2-methoxy-4-(methylsulfinyl)phenyl]-4-methyl-5-(3-pyridyl)imidazole.
mp: 90°–95° C.
IR (Nujol): 1600, 1565 cm$^{-1}$.
NMR (DMSO-d$_6$, δ): 2.24 (3H, s), 2.53 (3H, s), 3.81 (3H, s), 6.7–7.0 (2H, m), 7.43 (1H, dd, J=8 Hz, 4 Hz), 7.62 (1H, d, J=8 Hz), 7.92 (1H, ddd, J=8 Hz, 2 Hz, 2 Hz), 8.48 (1H, dd, J=2 Hz, 4 Hz), 8.69 (1H, d, J=2 Hz).

EXAMPLE 24

1-Hydroxy-2-(2,4-dimethoxyphenyl)-4-methyl-5-(3-pyridyl)imidazole.
mp: 110°–120° C.
IR (Nujol): 1610 cm$^{-1}$.
NMR (DMSO-d$_6$, δ): 2.16 (3H, s), 3.70 (3H, s), 3.77 (3H, s), 6.2–6.5 (2H, m), 7.0–7.4 (1H, m), 7.91 (1H, dd, J=2 Hz, 8 Hz), 7.98 (1H, d, J=9 Hz), 8.43 (1H, dd, J=2 Hz, 5 Hz), 8.56 (1H, d, J=2 Hz).

EXAMPLE 25

2-(2-Fluorophenyl)-1-hydroxy-4-methyl-5-(3-pyridyl)imidazole.
mp: 76°–82° C.
IR (Nujol): 1585, 1630, 1500 cm$^{-1}$.
NMR (DMSO-d$_6$, δ): 2.30 (3H, s), 7.2–7.85 (5H, m), 8.00 (1H, ddd, J=8 Hz, 2 Hz, 2 Hz), 8.60 (1H, dd, J=5 Hz, 2Hz), 8.80 (1H, d, J=2 Hz).

EXAMPLE 26

2-(4-Fluorophenyl)-1-hydroxy-4-methyl-5-(3-pyridyl)imidazole
mp: 101°–102° C.
NMR (DMSO-d$_6$, δ): 2.23 (3H, s), 7.12–7.56 (3H, m), 7.80–8.30 (3H, m), 8.56 (1H, d, J=5 Hz), 8.74 (1H, s).

EXAMPLE 27

2-(3-Chlorophenyl)-1-hydroxy-4-methyl-5-(3-pyridyl)imidazole.
mp: 74°–84° C.
IR (Nujol): 1598, 1567 cm$^{-1}$.
NMR (DMSO-d$_6$, δ): 2.25 (3H, s), 7.4–7.65 (3H, m), 7.88–8.2 (3H, m), 8.60 (1H, d, J=5 Hz), 8.78 (1H, s).

EXAMPLE 28

2-(2-Chlorophenyl)-1-hydroxy-4-methyl-5-(3-pyridyl)imidazole.
mp: 105°–112° C.
IR (Nujol): 1600, 1565 cm$^{-1}$.
NMR (DMSO-d$_6$, δ): 2.28 (3H, s), 7.3–7.7 (5H, m), 7.95 (1H, ddd, J=8 Hz, 2 Hz, 2 Hz), 8.3–8.8 (2H, m).

EXAMPLE 29

2-(4-Chlorophenyl)-1-hydroxy-4-methyl-5-(3-pyridyl)imidazole.
mp: 108°–110° C.
IR (Nujol): 1640, 1600, 1500 cm$^{-1}$.
NMR (DMSO-d$_6$, δ): 2.32 (3H, s), 7.4–7.75 (3H, m), 7.85–8.3 (3H, m), 8.62 (1H, dd, J=5 Hz, 2 Hz), 8.78 (1H, d, J=2 Hz).

EXAMPLE 30

2-(3,4-Dichlorophenyl)-1-hydroxy-4-methyl-5-(3-pyridyl)imidazole.
mp: 139°–145° C.
IR (Nujol): 1635, 1496 cm$^{-1}$.
NMR (DMSO-d$_6$, δ): 2.4 (3H, s), 7.56 (1H, dd, J=8 Hz, 5 Hz), 7.78 (1H, d, J=8 Hz), 7.9–8.2 (2H, m), 8.33 (1H, d, J=2 Hz), 8.68 (1H, dd, J=5 Hz, 2 Hz), 8.8 (1H, d, J=2 Hz).

EXAMPLE 31

1-Hydroxy-2-(2,4-dichlorophenyl)-4-methyl-5-(3-pyridyl)imidazole.
mp: 104°–108° C.
IR (Nujol): 1596, 1552 cm$^{-1}$.
NMR (DMSO-d$_6$, δ): 2.32 (3H, s), 7.42–7.89 (4H, m), 8.07 (1H, ddd, J=8 Hz, 2 Hz, 2 Hz), 8.67 (1H, dd, J=5 Hz, 2 Hz), 8.86 (1H, d, J=2 Hz).

EXAMPLE 32

2-(4-Dimethylamino-2-methoxyphenyl)-1-hydroxy-4-methyl-5-(3-pyridyl)imidazole.
mp: 96°–98° C.
IR (Nujol): 1607, 1611, 1562 cm$^{-1}$.
NMR (DMSO-d$_6$, δ): 2.24 (3H, s), 2.96 (6H, s), 3.82 (3H, s), 6.15–6.46 (2H, m), 7.28–7.78 (2H, m), 7.98 (1H, ddd, J=8 Hz, 2 Hz, 2 Hz), 8.52 (1H, dd, J=5 Hz, 2 Hz), 8.77 (1H, d, J=2 Hz).

EXAMPLE 33

1-Hydroxy-2-(3-hydroxy-4-methoxyphenyl)-4-methyl-5-(3-pyridyl)imidazole.
NMR (DMSO-d$_6$, δ): 2.18 (3H, s), 3.75 (3H, s), 6.86 (2H, d, J=8 Hz), 7.25–7.52 (2H, m), 7.60 (1H, s), 7.88 (1H, ddd, J=8 Hz, 2 Hz, 2 Hz), 8.43 (1H, dd, J=5 Hz, 2 Hz), 8.66 (1H, d, J=2 Hz).

EXAMPLE 34

2-(5-Chloro-2-methoxyphenyl)-1-hydroxy-4-methyl-5-(3-pyridyl)imidazole.
mp: 81°–83° C.
IR (Nujol): 1673, 1596, 1483 cm$^{-1}$.
NMR (DMSO-d$_6$, δ): 2.26 (3H, s), 3.78 (3H, s), 7.08 (1H, d, J=8 Hz), 7.25–7.52 (3H, m), 7.91 (1H, d, J=8 Hz), 8.47 (1H, d, J=5 Hz), 8.69 (1H, s).

EXAMPLE 35

1-Hydroxy-4-methyl-2-(2-methoxy-5-nitrophenyl)-5-(3-pyridyl)imidazole.
mp: 151°–155° C.
IR (Nujol: 1611, 1586, 1538, 1515 cm$^{-1}$.
NMR (DMSO-d$_6$, δ): 2.30 (3H, s), 3.98 (3H, s), 7.36 (1H, d, J=9 Hz), 7.48 (1H, dd, J=8 Hz, 5 Hz), 8.01 (1H, ddd, J=8 Hz, 2 Hz, 2 Hz), 8.34 (1H, dd, J=8 Hz, 2 Hz), 8.57 (1H, dd, J=5 Hz, 2 Hz), 8.75 (1H, d, J=2 Hz).

EXAMPLE 36

1-Hydroxy-4-methyl-2-(2-methoxy-3-nitrophenyl)-5-(3-pyridyl)imidazole.
mp: 106°–111° C.
IR (Nujol): 1536 cm$^{-1}$.
NMR (DMSO-d$_6$, δ): 2.30 (3H, s), 3.71 (3H, s), 7.31–8.15 (4H, m), 8.42–8.67 (2H, m), 8.31 (1H, s), 11.72 (1H, br s).

EXAMPLE 37

2-(5-Chloro-2,4-dimethoxyphenyl)-1-hydroxy-4-methyl-5-(3-pyridyl)imidazole.
mp: 146°–149° C.
IR (Nujol): 1610 cm$^{-1}$.
NMR (DMSO-d$_6$, δ): 2.25 (3H, s), 3.86 (3H, s), 3.96 (3H, s), 6.86 (1H, s), 7.46 (1H, dd, J=8 Hz, J=4 Hz), 7.80 (1H, br s), 7.97 (1H, ddd, J=8 Hz, J=2 Hz, J=2 Hz), 8.52 (1H, dd, J=4 Hz, J=2 Hz), 8.73 (1H, d, J=2 Hz).
Mass (M/Z): 345 (M+).

EXAMPLE 38

2-(3-Chloro-4,5-dimethoxyphenyl)-1-hydroxy-4-methyl-5-(3-pyridyl)imidazole.
mp: 123°–132° C.
IR (Nujol): 1598, 1565 cm$^{-1}$.
NMR (DMSO-d$_6$, δ): 2.20 (3H, s), 3.76 (3H, s), 3.78 (3H, s), 7.25–8.08 (4H, m), 8.45 (1H, d, J=5 Hz), 8.69 (1H, s).

EXAMPLE 39

2-(3-Chloro-4-hydroxy-5-methoxyphenyl)-1-hydroxy-4-methyl-5-(3-pyridyl)imidazole.
mp: 190°–195° C.
IR (Nujol): 1573, 1504 cm$^{-1}$.
NMR (DMSO-d$_6$, δ): 2.21 (3H, s), 3.82 (3H, s), 7.3–7.7 (3H, m), 7.88 (1H, d, J=8 Hz), 8.46 (1H, s), 8.66 (1H, s).

EXAMPLE 40

1-Hydroxy-2-(4-hydroxy-3-methoxyphenyl)-4-methyl-5-(3-pyridyl)imidazole.
mp: 152°–155° C.
IR (Nujol): 1595, 1511 cm$^{-1}$.
NMR (DMSO-d$_6$, δ): 2.21 (3H, s), 3.76 (3H, s), 6.78 (1H, d, J=8 Hz), 7.22–7.66 (3H, m), 7.87 (1H, d, J=8 Hz), 8.45 (1H, d, J=5 Hz), 8.65 (1H, s).

EXAMPLE 41

1-Hydroxy-4-methyl-2-(2-nitrophenyl)-5-(3-pyridyl)imidazole.
mp: 135°–145° C.
IR (Nujol): 1613, 1530 cm$^{-1}$.
NMR (DMSO-d$_6$, δ): 2.30 (3H, s), 7.52 (1H, dd, J=8 Hz, 8 Hz), 7.7–8.3 (5H, m), 8.58 (1H, dd, J=8 Hz, 2 Hz), 8.75 (1H, d, J=2 Hz).

EXAMPLE 42

2-[4-(N-Acetyl-N-methylamino)-5-chloro-2-methoxyphenyl]-1-hydroxy-4-methyl-5-(3-pyridyl)imidazole.
mp: 222°–224° C.
IR (Nujol): 1662, 1600, 1492 cm$^{-1}$.
NMR (DMSO-d$_6$, δ): 2.31 (3H, s), 2.80 (3H, s), 3.15 (3H, s), 3.59 (3H, s), 7.35–7.62 (2H, m), 7.82–8.2 (2H, m), 8.58 (1H, dd, J=5 Hz, 2 Hz), 8.77 (1H, d, J=2 Hz).
Mass (M/Z): 385 (M+).

EXAMPLE 43

1-Hydroxy-4-methyl-2-(o-tolyl)-5-(3pyridyl)imidazole.
mp: 90°–95° C.
IR (Nujol): 1565 cm$^{-1}$.
NMR (DMSO-d$_6$, δ): 2.25 (3H, s), 2.35 (3H, s), 7.25–7.66 (5H, m), 7.95 (1H, ddd, J=8 Hz, 2 Hz, 2 Hz), 8.56 (1H, dd, J=5 Hz, 2 Hz), 8.78 (1H, d, J=2 Hz).

EXAMPLE 44

1-Hydroxy-2-(2-methoxy-4-methylsulfinylphenyl)-5-methyl-4-(4-pyridyl)imidazole.
mp: 205°–208° C.
IR (Nujol): 1600 cm$^{-1}$.
NMR (DMSO-d$_6$, δ): 2.47 (3H, s), 2.54 (3H, s), 3.81 (3H, s), 6.93 (1H, d, J=8 Hz), 7.0 (1H, s), 7.35 (1H, d, J=8 Hz), 7.66 (2H, d, J=8 Hz), 8.54 (2H, d, J=8 Hz).

EXAMPLE 45

1-Hydroxy-2-(3-methoxy-4-methylthiophenyl)-5-methyl-4-(4-pyridyl)imidazole.
mp: 252°–257° C.
IR (Nujol): 1610 cm$^{-1}$.
NMR (DMSO-d$_6$, δ): 2.46 (3H, s), 2.52 (3H, s), 3.92 (3H, s), 7.26 (1H, d, J=8 Hz), 7.9–7.6 (4H, m), 8.7–8.5 (2H, m).

EXAMPLE 46

2-(2,6-Dimethoxyphenyl)-1-hydroxy-4-methyl-5-(3-pyridyl)imidazole.

mp: 236°–239° C.
IR (Nujol): 1590 cm$^{-1}$.
NMR (DMSO-d$_6$, δ): 2.25 (3H, s), 3.71 (6H, s), 6.73 (2H, d, J=8 Hz), 7.6–7.2 (2H, m), 7.96 (1H, ddd, J=8 Hz, J=2 Hz, J=2 Hz), 8.48 (1H, dd, J=5 Hz, J=2 Hz), 8.75 (1H, d, J=2 Hz), 11.1 (1H, br s).

EXAMPLE 47

1-Hydroxy-2-(3-methoxy-4-methylthiophenyl)-4-methyl-5-(3-pyridyl)imidazole.
mp: 145°–150° C.
IR (Nujol): 1630, 1600, 1565 cm$^{-1}$.
NMR (DMSO-d$_6$, δ): 2.24 (3H, s), 2.43 (3H, s), 3.86 (3H, s), 7.22 (1H, d, J=8 Hz), 7.50 (1H, dd, J=8 Hz, J=5 Hz), 7.9–7.65 (2H, m), 7.95 (1H, ddd, J=8 Hz, J=2 Hz, J=2 Hz), 8.56 (1H, dd, J=5 Hz, J=2 Hz), 8.78 (1H, d, J=2 Hz).

EXAMPLE 48

2-(4-Ethoxy-2-methoxyphenyl)-1-hydroxy-4-methyl-5-(3-pyridyl)imidazole.
mp: 90°–95° C.
IR (Nujol): 1615, 1580 cm$^{-1}$.
NMR (DMSO-d$_6$, δ): 1.35 (3H, t, J=7 Hz), 2.24 (3H, s), 3.78 (3H, s), 4.10 (2H, q, J=7 Hz), 6.57 (1H, dd, J=8 Hz, J=2 Hz), 6.64 (1H, d, J=2 Hz), 7.7–7.4 (2H, m), 7.98 (1H, ddd, J=8 Hz, J=2 Hz, J=2 Hz), 8.51 (1H, dd, J=4 Hz, J=2 Hz), 8.76 (1H, d, J=2 Hz).

EXAMPLE 49

2-(4-Benzyloxy-2-methoxyphenyl)-1-hydroxy-4-methyl-5-(3-pyridyl)imidazole.
mp: 191°–193° C.
IR (Nujol): 1615, 1580 cm$^{-1}$.
NMR (DMSO-d$_6$, δ): 2.25 (3H, s), 3.78 (3H, s), 5.17 (2H, s), 6.68 (1H, dd, J=2 Hz, J=8 Hz), 6.77 (1H, d, J=2 Hz), 7.7–7.3 (7H, m), 7.98 (1H, ddd, J=2 Hz, J=2 Hz, J=8 Hz), 8.54 (1H, dd, J=2 Hz, J=5 Hz), 8.77 (1H, d, J=2 Hz), 11.4 (1H, br s).

EXAMPLE 50

1-Hydroxy-4-methyl-5-(3-pyridyl)-2-(2,4,5-trimethoxyphenyl)imidazole.
mp: 80°–90° C.
IR (Nujol): 1615 cm$^{-1}$.
NMR (DMSO-d$_6$, δ): 2.25 (3H, s), 3.64 (3H, s), 3.79 (3H, s), 3.84 (3H, s), 6.78 (1H, s), 7.50 (1H, br s), 7.46 (1H, dd, J=4 Hz, J=8 Hz), 7.99 (1H, ddd, J=2 Hz, J=2 Hz, J=8 Hz), 8.53 (1H, dd, J=2 Hz, J=4 Hz), 8.77 (1H, d, J=2 Hz), 11.5 (1H, br s).
Mass (M/Z): 341 (M$^+$).

EXAMPLE 51

1-Hydroxy-4-methyl-5-(3-pyridyl)-2-(2,4,6-trimethoxyphenyl)imidazole.
mp: 197°–199° C.
IR (Nujol): 1615, 1590 cm$^{-1}$.
NMR (DMSO-d$_6$, δ): 2.22 (3H, s), 3.66 (6H, s), 3.82 (3H, s), 6.29 (2H, s), 7.45 (1H, dd, J=8 Hz, J=5 Hz), 7.97 (1H, ddd, J=8 Hz, J=2 Hz, J=2 Hz), 8.50 (1H, dd, J=5 Hz, J=2 Hz), 8.76 (1H, d, J=2 Hz), 11.0 (1H, br s).

EXAMPLE 52

1-Hydroxy-2-(4-methoxyphenyl)-4-methyl-5-(3-pyridyl)imidazole.
mp: 95°–100° C.
IR (Nujol): 1610 cm$^{-1}$.
NMR (CDCl$_3$, δ): 1.93 (3H, s), 3.71 (3H, s), 6.68 (2H, d, J=9 Hz), 7.18 (1H, dd, J=5 Hz, J=8 Hz), 7.5–8.0 (4H, m), 8.33 (1H, dd, J=5 Hz, J=2 Hz), 8.45 (1H, d, J=2 Hz).

EXAMPLE 53

2-(5-Chloro-2-methoxy-4-methylphenyl)-1-hydroxy-4-methyl-5-(3-pyridyl)imidazole.
mp: 130°–135° C.
IR (Nujol): 1630, 1565 cm$^{-1}$.
NMR (DMSO-d$_6$, δ): 2.25 (3H, s), 2.36 (3H, s), 3.79 (3H, s), 7.09 (1H, s), 7.40 (1H, br s), 7.41 (1H, dd, J=8 Hz, J=5 Hz), 7.93 (1H, ddd, J=8 Hz, J=2 Hz, J=2 Hz), 8.45 (1H, dd, J=5 Hz, J=2 Hz), 8.69 (1H, d, J=2 Hz), 11.40 (1H, br s).

EXAPLE 54

2-(3,4-Dimethoxyphenyl)-4-methyl-5-(3-pyridyl)imidazole.
mp: 246°–248° C.
IR (Nujol): 1600, 1500 cm$^{-1}$.
NMR (DMSO-d$_6$, δ): 2.53 (3H, s), 3.82 (3H, s), 3.85 (3H, s), 7.04 (1H, d, J=9 Hz), 7.2–7.7 (3H, m), 8.10 (1H, br d, J=8 Hz), 8.45 (1H, br d, J=6 Hz), 8.92 (1H, br s).

EXAMPLE 55

2-(3,4-Dimethoxyphenyl)-5-methyl-4-(2-pyridyl)imidazole.
mp: 96°–98° C.
IR (Nujol): 3300, 1720, 1590, 1500, 1260 cm$^{-1}$.
NMR (CDCl$_3$, δ): 2.62 (3H, s), 3.77 (3H, s), 3.86 (3H, s), 6.18 (1H, d, J=8 Hz), 6.9–7.1 (1H, m), 7.39 (1H, dd, J=2 Hz, 8 Hz), 7.44 (1H, s), 7.5–7.7 (2H, m), 8.40 (1H, d, J=5 Hz).

EXAMPLE 56

2-(3,4-Dimethoxyphenyl)-4-(2-pyridyl)imidazole.
mp: 80°–82° C.
IR (Nujol): 1680, 1590, 1490 cm$^{-1}$.
NMR (CDCl$_3$, δ): 3.83 (3H, s), 3.87 (3H, s), 6.81 (1H, d, J=8 Hz), 7.0–7.2 (1H, m), 7.36 (1H, dd, J=2 Hz, 8 Hz), 7.48 (1H, d, J=2 Hz), 7.60 (1H, s), 7.6–7.8 (2H, m), 8.42 (1H, d, J=6 Hz).
Mass (m/e): 281 (M$^+$).

EXAMPLE 57

2-(3,4-Dimethoxyphenyl)-5-methyl-4-(4-pyridyl)imidazole.
mp: 234°–236° C.
IR (Nujol): 1600 cm$^{-1}$.
NMR (CDCl$_3$-CD$_3$OD, δ): 2.50 (3H, s), 3.86 (3H, s), 3.91 (3H, s), 6.86 (1H, d, J=8 Hz), 7.3–7.7 (4H, m), 8.42 (2H, d, J=6 Hz).

EXAMPLE 58

2-(3,4-Dimethoxyphenyl)-5-ethyl-4-(4-pyridyl)imidazole.
mp: 181°–182° C. (dec.).
IR (Nujol): 1595, 1530, 1410 cm$^{-1}$.
NMR (CDCl$_3$, δ): 1.31 (3H, t, J=7.5 Hz), 2.85 (2H, q, J=7.5 Hz), 3.83 (6H, s), 6.77 (1H, d, J=9 Hz), 7.37 (1H, dd, J=2 Hz, 9 Hz), 7.49 (1H, d, J=2 Hz), 7.54, 8.44 (4H, ABq, J=6 Hz).
Mass (m/e): 309 (M$^+$).

EXAMPLE 59

2-(2,4-Dimethoxyphenyl)-5-methyl-4-(2-pyridyl)imidazole.

mp: 118°–120° C.
IR (Nujol): 3260, 1610, 1580, 1490 cm$^{-1}$.
NMR (CDCl$_3$, δ): 2.64 (3H, s), 3.84 (3H, s), 4.01 (3H, s), 6.53 (1H, s), 6.57 (1H, dd, J=2 Hz, 9 Hz), 7.01 (1H, dd, J=6 Hz, 10 Hz), 7.5–7.8 (2H, m), 8.23 (1H, d, J=10 Hz), 8.50 (1H, d, J=6 Hz).

EXAMPLE 60

2-(3,4-Dimethoxyphenyl)-5-ethyl-4-(2-pyridyl)imidazole.
mp: 160°–163° C.
IR (Nujol): 1590, 1500, 1270, 1015 cm$^{-1}$.
NMR (CDCl$_3$, δ): 1.35 (3H, t, J=8 Hz), 2.99 (2H, t, J=8 Hz), 3.85 (6H, s), 6.80 (1H, d, J=9 Hz), 6.9–7.1 (1H, m), 7.33 (1H, dd, J=2 Hz, 9 Hz), 7.43 (1H, d, J=2 Hz), 7.5–7.7 (2H, m), 8.43 (1H, d, J=5 Hz).

EXAMPLE 61

2-(2,4-Dimethoxyphenyl)-5-methyl-4-(4-pyridyl)imidazole.
mp: 224°–226° C.
IR (Nujol): 1605 cm$^{-1}$.
NMR (DMSO-d$_6$, δ): 2.56 (3H, s), 3.85 (3H, s), 3.96 (3H, s), 6.6–6.8 (2H, m), 7.73 (2H, d, J=6 Hz), 8.07 (1H, d, J=9 Hz), 8.58 (2H, d, J=6 Hz), 11–12 (1H, br s).

EXAMPLE 62

2-(2,4-Dimethoxyphenyl)-5-ethyl-4-(4-pyridyl)imidazole.
mp: 212°–213° C.
IR (Nujol): 1595, 1530, 1505 cm$^{-1}$.
NMR (CDCl$_3$, δ): 1.36 (3H, t, J=8 Hz), 2.93 (2H, q, J=8 Hz), 3.83 (3H, s), 3.97 (3H, s), 6.51 (1H, d, J=2 Hz), 6.57 (1H, dd, J=2 Hz, 10 Hz), 7.52 (2H, dd, J=2 Hz, 6 Hz), 8.23 (1H, d, J=10 Hz), 8.50 (1H, dd, J=2 Hz, 6 Hz).
Mass (m/e): 309 (M+).

EXAMPLE 63

2-(2-Methoxyphenyl)-5-methyl-4-(3-pyridyl)imidazole.
mp: 198°–200° C.
IR (Nujol): 1600, 1585, 1560 cm$^{-1}$.
NMR (DMSO-d$_6$, δ): 2.55 (3H, s), 3.99 (3H, s), 7.6–6.9 (4H, m), 8.0–8.3 (2H, m), 8.46 (1H, dd, J=2 Hz, 5 Hz), 8.98 (1H, d, J=2 Hz), 11.7 (1H, br s).

EXAMPLE 64

2-(2,4-Dimethoxyphenyl)-5-methyl-4-(3-pyridyl)imidazole.
mp: 164°–166° C.
IR (Nujol): 1615, 1590 cm$^{-1}$.
NMR (DMSO-d$_6$, δ): 2.47 (3H, s), 3.80 (3H, s), 3.93 (3H, s), 6.64 (1H, dd, J=2 Hz, 8 Hz), 6.68 (1H, d, J=2 Hz), 7.40 (1H, dd, J=5 Hz, 8 Hz), 7.9–8.2 (2H, m), 8.43 (1H, br d, J=5 Hz), 8.94 (1H, br s), 11.5 (1H, br s).

EXAMPLE 65

2-(2,4-Dimethoxyphenyl)-4-ethyl-5-(3-pyridyl)imidazole
mp: 148°–151° C.
IR (Nujol): 1618, 1590, 1495 cm$^{-1}$.
NMR (DMSO-d$_6$, δ): 1.25 (3H, t, J=8 Hz), 2.85 (2H, q, J=8 Hz), 3.80 (3H, s), 3.91 (3H, s), 6.49–6.65 (2H, m), 6.63 (1H, s), 7.35 (1H, dd, J=8 Hz, 4 Hz), 7.82–8.01 (2H, m), 8.35 (1H, m), 8.79 (1H, br s).

EXAMPLE 66

2-(2,5-Dimethoxyphenyl)-5-methyl-4-(3-pyridyl)imidazole
mp: 152°–154° C.
IR (Nujol): 1590 cm$^{-1}$.
NMR (DMSO-d$_6$, δ): 2.53 (3H, s), 3.78 (3H, s), 3.91 (3H, s), 6.88 (1H, dd, J=8 Hz, 2 Hz), 7.10 (1H, d, J=8 Hz), 7.40 (1H, dd, J=4 Hz, 8 Hz), 7.68 (1H, d, J=2 Hz), 8.07 (1H, ddd, J=8 Hz, 2 Hz, 2 Hz), 8.44 (1H, br d, J=4 Hz), 8.97 (1H, br s).

EXAMPLE 67

2-(2,3-Dimethoxyphenyl)-5-methyl-4-(3-pyridyl)imidazole.
mp: 125°–127° C.
IR (Nujol): 1590, 1555 cm$^{-1}$.
NMR (DMSO-d$_6$, δ): 2.50 (3H, s), 3.77 (3H, s), 3.84 (3H, s), 6.96 (1H, dd, J=8 Hz, 2 Hz), 7.06 (1H, dd, J=8 Hz, 8 Hz), 7.32 (1H, dd, J=8 Hz, 4 Hz), 7.54 (1H, dd, J=2 Hz, 8 Hz), 7.97 (1H, ddd, J=2 Hz, 2 Hz, 8 Hz), 8.33 (1H, br d, J=4 Hz), 8.83 (1H, br s), 11.73 (1H, br s).

EXAMPLE 68

2-(2,3,4-Trimethoxyphenyl)-5-methyl-4-(3-pyridyl)imidazole.
mp: 144°–146° C.
IR (Nujol): 1600 cm$^{-1}$.
NMR (DMSO-d$_6$, δ): 2.47 (3H, s), 3.78 (3H, s), 3.81 (3H, s), 3.83 (3H, s), 6.84 (1H, d, J=9 Hz), 7.32 (1H, dd, J=8 Hz, 4 Hz), 7.62 (1H, d, J=9 Hz), 7.96 (1H, br d, J=8 Hz), 8.32 (1H, br d, J=4 Hz), 8.82 (1H, br s), 11.62 (1H, br s).

EXAMPLE 69

2-(3,4,5-Trimethoxyphenyl)-5-methyl-4-(3-pyridyl)imidazole.
mp: 258°–260° C.
IR (Nujol): 1590 cm$^{-1}$.
NMR (CDCl$_3$-CD$_3$OD, δ): 2.45 (3H, s), 3.84 (3H, s), 3.90 (6H, s), 7.18 (2H, s), 7.33 (1H, dd, J=8 Hz, 5 Hz), 7.96 (1H, ddd, J=8 Hz, 2 Hz, 2 Hz), 8.34 (1H, br d, J=5 Hz), 8.72 (1H, br s).

EXAMPLE 70

2-(4-Chloro-2-methoxyphenyl)-5-methyl-4-(3-pyridyl)imidazole.
mp: 145°–147° C.
IR (Nujol): 1585, 1595 cm$^{-1}$.
NMR (DMSO-d$_6$, δ): 2.54 (3H, s), 4.01 (3H, s), 7.12 (1H, dd, J=8 Hz, 2 Hz), 7.25 (1H, d, J=2 Hz), 7.43 (1H, dd, J=8 Hz, 5 Hz), 8.08 (1H, ddd, J=8 Hz, 2 Hz, 2 Hz), 8.16 (1H, d, J=8 Hz), 8.47 (1H, dd, J=2 Hz, 5 Hz), 8.99 (1H, d, J=2 Hz), 11.75 (1H, br s).

EXAMPLE 71

2-(4-Acetamido-5-chloro-2-methoxyphenyl)-5-methyl-4-(3-pyridyl)imidazole.
mp: 239°–240° C.
IR (Nujol): 3400, 1680, 1590, 1520, 1490 cm$^{-1}$.
NMR (DMSO-d$_6$, δ): 2.14 (3H, s), 2.50 (3H, s), 3.91 (3H, s), 7.35 (1H, dd, J=5 Hz, 8 Hz), 7.63 (1H, s), 8.02 (1H, s), 8.02 (1H, dt, J=2 Hz, 8 Hz), 8.35 (1H, dd, J=2 Hz, 5 Hz), 8.82 (1H, d, J=2 Hz), 9.40 (1H, s), 11.63 (1H, s).
Mass (m/e): 356 (M+).

EXAMPLE 72

2-(4-Acetamido-2-methoxyphenyl)-5-methyl-4-(3-pyridyl)imidazole.
mp: 215°–218° C.
IR (Nujol): 1675, 1600 cm$^{-1}$.
NMR (DMSO-d$_6$, δ): 2.06 (3H, s), 2.49 (3H, s), 3.90 (3H, s), 7.14 (1H, dd, J=8 Hz, 2 Hz), 7.33 (1H, dd, J=8 Hz, 5 Hz), 7.48 (1H, d, J=2 Hz), 7.92 (1H, d, J=8 Hz), 7.96 (1H, ddd, J=8 Hz, 2 Hz, 2 Hz), 8.33 (1H, br d, J=5 Hz), 8.82 (1H, br s), 9.99 (1H, s), 11.45 (1H, br s).

EXAMPLE 73

2-Phenyl-5-methyl-4-(3-pyridyl)imidazole.
mp: 206°–208° C.
IR (Nujol): 1600, 1590, 1575 cm$^{-1}$.
NMR (DMSO-d$_6$, δ): 2.48 (3H, s), 7.2–7.6 (4H, m), 7.8–8.1 (3H, m), 8.35 (1H, br d, J=4 Hz), 8.83 (1H, br s), 12.39 (1H, br s).

EXAMPLE 74

2-(2-Methoxy-4-nitrophenyl)-4-methyl-5-(3-pyridyl)imidazole.
mp: 203°–207° C.
IR (Nujol): 1580 cm$^{-1}$.
NMR (DMSO-d$_6$, δ): 2.58 (3H, s), 4.11 (3H, s), 7.37 (1H, m), 7.75–8.14 (4H, m), 8.37 (1H, m), 8.88 (1H, br s), 11.93 (1H, br s).

EXAMPLE 75

2-(2-Methoxy-4-methylthiophenyl)-5-methyl-4-(3-pyridyl)imidazole.
mp: 153°–156° C.
IR (Nujol): 1600, 1580, 1565 cm$^{-1}$.
NMR (DMSO-d$_6$, δ): 2.48 (3H, s), 2.52 (3H, s), 3.94 (3H, s), 6.89 (1H, dd, J=8 Hz), 2 Hz), 6.94 (1H, d, J=2 Hz), 7.34 (1H, dd, J=8 Hz, J=4 Hz), 7.96 (1H, d, J=8 Hz), 7.98 (1H, ddd, J=8 Hz, 2 Hz, 2 Hz), 8.34 (1H, dd, J=4 Hz, 2 Hz), 8.84 (1H, d, J=2 Hz), 11.45 (1H, br s).

EXAMPLE 76

2-(2,4-Dimethoxyphenyl)-5-hydroxymethyl-4-(3-pyridyl)imidazole.
mp: 192°–195° C.
IR (Nujol): 1615, 1595 cm$^{-1}$.
NMR (DMSO-d$_6$, δ): 3.83 (3H, s), 3.97 (3H, s), 4.70 (2H, br s), 5.26 (1H, br s), 6.66 (1H, dd, J=7 Hz, 2 Hz), 6.74 (1H, d, J=2 Hz), 7.24 (1H, dd, J=5 Hz, 8 Hz), 7.9–8.3 (2H, m), 8.47 (1H, dd, J=2 Hz, 5 Hz), 9.02 (1H, br s).

EXAMPLE 77

2-(2-Methoxy-4-methylthiophenyl)-5-hydroxymethyl-4-(3-pyridyl)imidazole.
mp: 199°–201° C.
IR (Nujol): 1605, 1590, 1575 cm$^{-1}$.
NMR (DMSO-d$_6$, δ): 2.52 (3H, s), 3.94 (3H, s), 4.61 (2H, d, J=4 Hz), 5.20 (1H, br t, J=4 Hz), 6.88 (1H, dd, J=8 Hz, 2 Hz), 6.93 (1H, d, J=2 Hz), 7.35 (1H, dd, J=8 Hz, 4 Hz), 7.97 (1H, d, J=8 Hz), 8.06 (1H, ddd, J=8 Hz, 2 Hz, 2 Hz), 8.37 (1H, br d, J=4 Hz), 8.90 (1H, br s), 11.57 (1H, br s).

EXAMPLE 78

2-(4-Amino-5-chloro-2-methoxyphenyl)-5-methyl-4-(3-pyridyl)imidazole.
mp: 178°–180° C.
IR (Nujol): 3480, 3280, 3150, 1630, 1600, 1560 cm$^{-1}$.
NMR (DMSO-d$_6$, δ): 2.50 (3H, s), 3.87 (3H, s), 5.58 (2H, s), 6.52 (1H, s), 7.32 (1H, dd, J=5 Hz, 8 Hz), 7.80 (1H, s), 7.98 (1h, d t, J=2 Hz, 8 Hz), 8.34 (1H, dd, J=2 Hz, 5 Hz), 8.82 (1H, d, J=2 Hz), 11.30 (1H, br s).
Mass (m/e): 314 (M+).

EXAMPLE 79

2-(4-Amino-2-methoxyphenyl)-5-methyl-4-(3-pyridyl)imidazole.
mp: 95°–100° C.
IR (Nujol): 1615 cm$^{-1}$.
NMR (DMSO-d$_6$, δ): 2.45 (3H, s), 3.83 (3H, s), 5.32 (2H, br s), 6.18 (1H, dd, J=8 Hz, 2 Hz), 6.24 (1H, d, J=2 Hz), 7.30 (1H, dd, J=8 Hz, 4Hz), 7.67 (1H, d, J=8 Hz), 7.94 (1H, ddd, J=8 Hz, 2 Hz, 2 Hz), 8.30 (1H, dd, J=4 Hz, 2 Hz), 8.80 (1H, d, J=2 Hz), 11.13 (1H, br s).

EXAMPLE 80

2-(2,4-Dimethoxyphenyl)-1,5-dimethyl-4-(3-pyridyl)imidazole.
mp: 129°–131° C.
IR (Nujol): 1615, 1595, 1580 cm$^{-1}$.
NMR (DMSO-d$_6$, δ): 2.40 (3H, s), 3.30 (3H, s), 3.76 (3H, s), 3.80 (3H, s), 6.4–6.7 (2H, m), 7.20 (1H, d, J=8 Hz), 7.31 (1H, dd, J=4 Hz, 8 Hz), 7.89 (1H, br d, J=8 Hz), 8.32 (1H, br d, J=4 Hz), 8.74 (1H, br s).

EXAMPLE 81

2-(2-Methoxy-4-methylphenyl)-4-methyl-5-(3-pyridyl)imidazole.
mp: 125°–128° C.
IR (Nujol): 1615, 1590 cm$^{-1}$.

EXAMPLE 82

2-(3-Methoxy-4-methylthiophenyl)-4-methyl-5-(3-pyridyl)imidazole.
mp: 226°–228° C.
IR (Nujol): 1605, 1570 cm$^{-1}$.

EXAMPLE 83

2-(2,6-Dimethoxyphenyl)-4-methyl-5-(3-pyridyl)imidazole.
mp: 185°–187° C.
IR (Nujol): 1608, 1590 cm$^{-1}$.

EXAMPLE 84

2-(3-Methoxy-4-methylthiophenyl)-4-methyl-5-(4-pyridyl)imidazole.
mp: 283°–285° C.
IR (Nujol): 1600 cm$^{-1}$.

EXAMPLE 85

2-(2-Methoxy-4-methylthiophenyl)-4-methyl-5-(4-pyridyl)imidazole.
mp: 192°–194° C.
IR (Nujol): 1606, 1565 cm$^{-1}$.

EXAMPLE 86

4-Methyl-2-(2-nitrophenyl)-5-(3-pyridyl)imidazole.
mp: 229°–230° C.
IR (Nujol): 1613, 1601, 1578, 1539, 1497 cm$^{-1}$.

EXAMPLE 87

4-Methyl-2-(o-tolyl)-5-(3-pyridyl)imidazole.
mp: 129°–130° C.
IR (Nujol): 1604, 1570, 1494 cm$^{-1}$.

EXAMPLE 88

2-(4-Chlorophenyl)-4-methyl-5-(3-pyridyl)imidazole.
mp: 229°–231° C.
IR (Nujol): 1600, 1574, 1492 cm$^{-1}$.

EXAMPLE 89

2-[4-(N-Acetyl-N-methylamino)-5-chloro-2-methoxyphenyl]-4-methyl-5-(3-pyridyl)imidazole.
mp: 220°–221° C.
IR (Nujol): 1672, 1599, 1563, 1525, 1490 cm$^{-1}$.

EXAMPLE 90

2-(2-Chlorophenyl)-4-methyl-5-(3-pyridyl)imidazole.
mp: 108°–109° C.
IR (Nujol): 1590, 1562, 1480 cm$^{-1}$.

EXAMPLE 91

2-(3,4-Dichlorophenyl)-4-methyl-5-(3-pyridyl)imidazole.
mp: 269° C.
IR (Nujol): 1600, 1574 cm$^{-1}$.

EXAMPLE 92

2-(4-Fluorophenyl)-4-methyl-5-(3-pyridyl)imidazole.
mp: 123°–124° C.
IR (Nujol): 1600, 1570, 1539, 1502 cm$^{-1}$.

EXAMPLE 93

2-(3-Chlorophenyl)-4-methyl-5-(3-pyridyl)imidazole.
mp: 242°–243° C.
IR (Nujol): 1607, 1587, 1574, 1489 cm$^{-1}$.

EXAMPLE 94

2-(2-Fluorophenyl)-4-methyl-5-(3-pyridyl)imidazole.
mp: 194°–195° C.
IR (Nujol): 1599, 1590, 1567, 1525, 1485 cm$^{-1}$.

EXAMPLE 95

2-(2,4-Dichlorophenyl)-4-methyl-5-(3-pyridyl)imidazole.
mp: 160°–161° C.
IR (Nujol): 1590, 1569, 1556, 1484 cm$^{-1}$.

EXAMPLE 96

2-(5-Chloro-2,4-dimethoxyphenyl)-4-methyl-5-(3-pyridyl)imidazole.
mp: 241°–244° C.
IR (Nujol): 1610, 1590, 1565 cm$^{-1}$.

EXAMPLE 97

2-(5-Chloro-2-methoxy-4-methylphenyl)-4-methyl-5-(3-pyridyl)imidazole.
mp: 185°–187° C.
IR (Nujol): 1600, 1580, 1560 cm$^{-1}$.

EXAMPLE 98

2-(4-Methoxyphenyl)-4-methyl-5-(3-pyridyl)imidazole.
mp: 199°–201° C.
IR (Nujol): 1615, 1600 cm$^{-1}$.

EXAMPLE 99

4-Methyl-5-(3-pyridyl)-2-(2,4,6-trimethoxyphenyl)imidazole.
mp: 65°–75° C.
IR (Nujol): 1610, 1590 cm$^{-1}$.

EXAMPLE 100

4-Methyl-5-(3-pyridyl)-2-(2,4,5-trimethoxyphenyl)imidazole.
mp: 189°–191° C.
IR (Nujol): 1615, 1600 cm$^{-1}$.

EXAMPLE 101

2-(4-Benzyloxy-2-methoxyphenyl)-4-methyl-5-(3-pyridyl)imidazole.
mp: 160°–162° C.
IR (Nujol): 1615, 1590 cm$^{-1}$.

EXAMPLE 102

2-(4-Ethoxy-2-methoxyphenyl)-4-methyl-5-(3-pyridyl)imidazole.
mp: 151°–153° C.
IR (Nujol): 1615, 1590 cm$^{-1}$.

EXAMPLE 103

2-(5-Chloro-2-methoxyphenyl)-4-methyl-5-(3-pyridyl)imidazole.
mp: 193°–195° C.
IR (Nujol): 1600, 1586, 1565, 1619 cm$^{-1}$.

EXAMPLE 104

2-(4-Hydroxy-3-methoxyphenyl)-4-methyl-5-(3-pyridyl)imidazole.
mp: 278°–279° C.
IR (Nujol): 1609, 1575, 1508, 1490 cm$^{-1}$.

EXAMPLE 105

2-(3-Hydroxy-4-methoxyphenyl)-4-methyl-5-(3-pyridyl)imidazole.
mp: 267°–269° C.
IR (Nujol): 1595, 1574, 1505 cm$^{-1}$.

EXAMPLE 106

2-(3-Chloro-4,5-dimethoxyphenyl)-4-methyl-5-(3-pyridyl)imidazole.
mp: 215°–216° C.
IR (Nujol): 1573, 1497 cm$^{-1}$.

EXAMPLE 107

2-(3-Chloro-4-hydroxy-5-methoxyphenyl)-4-methyl-5-(3-pyridyl)imidazole.
mp: 251°–253° C.
IR (Nujol): 1575, 1504 cm$^{-1}$.

EXAMPLE 108

4-Methyl-2-(2-methoxy-5-nitrophenyl)-5-(3-pyridyl)imidazole.
mp: 220°–223° C.
IR (Nujol): 1593, 1534, 1508, 1490 cm$^{-1}$.

EXAMPLE 109

4-Methyl-2-(2-methoxy-3-nitrophenyl)-5-(3-pyridyl)imidazole.
mp: 145°–150° C.
IR (Nujol): 1600, 1566, 1535 cm$^{-1}$.

EXAMPLE 110

2-(2-Methoxy-4-methylsulfinylphenyl)-4-methyl-5-(3-pyridyl)imidazole.
IR (Nujol): 1660, 1600 cm$^{-1}$.

EXAMPLE 111

2-(2-Methoxy-4-methylsulfonylphenyl)-4-methyl-5-(3-pyridyl)imidazole.
mp: 115°–118° C.
IR (Nujol): 1600, 1590 cm$^{-1}$.

EXAMPLE 112

2-(2-Aminophenyl)-4-methyl-5-(3-pyridyl)imidazole.
mp: 221°–222° C.
IR (Nujol): 3450, 1618, 1602, 1573, 1600 cm$^{-1}$.

EXAMPLE 113

2-(5-Amino-2-methoxyphenyl)-4-methyl-5-(3-pyridyl)imidazole.
mp: 172°–173° C.
IR (Nujol): 3430, 1598, 1569, 1530, 1495 cm$^{-1}$.

EXAMPLE 114

4-Methyl-2-(4-methylamino-2-methoxyphenyl)-5-(3-pyridyl)imidazole.
mp: 54°–56° C.
IR (Nujol): 1612, 1580, 1560, cm$^{-1}$.

EXAMPLE 115

2-(2-Acetamidophenyl)-4-methyl-5-(3-pyridyl)imidazole.
mp: 270°–271° C.
IR (Nujol): 1700, 1620, 1598, 1580, 1545, 1495 cm$^{-1}$.

EXAMPLE 116

4Methyl-2-[2-(3-methylureido)phenyl]-5-(3-pyridyl)imidazole.
mp: 230°–231° C.
IR (Nujol): 3270, 1684, 1658, 1618, 1589, 1493 cm$^{-1}$.

EXAMPLE 117

2-(4-Hydroxy-2-methoxyphenyl)-4-methyl-5-(3-pyridyl)imidazole.
mp: 237°–240° C.
IR (Nujol): 1610 cm$^{-1}$.

EXAMPLE 118

2-(5-Bromo-2,4-dimethoxyphenyl)-4-methyl-5-(3-pyridyl)imidazole.
mp: 246°–248° C.
IR (Nujol): 1600, 1580 cm$^{-1}$.

EXAMPLE 119

2-(5-Chloro-4-methylamino-2-methoxyphenyl)-4-methyl-5-(3-pyridyl)imidazole.
mp: 205°–206° C.
IR (Nujol): 1616, 1570, 1546, 1498 cm$^{-1}$.

EXAMPLE 120

To a suspension of 1-hydroxy-2-(3,4-dimethoxyphenyl)-4-methyl-5-(3-pyridyl)imidazole (0.68 g) in methylene chloride (9 ml) was added phosphorus trichloride (0.76 ml) at ambient temperature. The mixture was refluxed for 1 hour, and cooled. The mixture was adjusted to pH 7.8 with aqueous sodium carbonate. The organic layer was separated, washed with brine, dried over magnesium sulfate, and evaporated. The residue was triturated with diisopropyl ether to give 2-(3,4-dimethoxyphenyl)-4-methyl-5-(3-pyridyl)imidazole (0.39 g).
mp: 246°–248° C.
IR (Nujol): 1600, 1500 cm$^{-1}$.
NMR (DMSO-d$_6$, δ): 2.53 (3H, s), 3.82 (3H, s), 3.85 (3H, s), 7.04 (1H, d, J=9 Hz), 7.2–7.7 (3H, m), 8.10 (1H, br d, J=8 Hz), 8.45 (1H, br d, J=6 Hz), 8.92 (1H, br s).

EXAMPLE 121

To a solution of 1-hydroxy-2-(2-methoxyphenyl)-4-methyl-5-(3-pyridyl)imidazole (0.5 g) in N,N-dimethylformamide (10 ml) was added phosphorus trichloride (0.31 ml) under ice-cooling. The mixture was stirred for 2 hours at 5° to 10° C. The mixture was poured into water (100 ml), and neutralized with aqueous sodium bicarbonate. The precipitate was collected, washed with water, and dried to give 2-(2-methoxyphenyl)-5-methyl-4-(3-pyridyl)imidazole (0.31 g).
mp: 198°–200° C.
IR (Nujol): 1600, 1585, 1560 cm$^{-1}$.
NMR (DMSO-d$_6$, δ): 2.55 (3H, s), 3.99 (3H, s), 6.9–7.6 (4H, m), 8.0–8.3 (2H, m), 8.46 (1H, dd, J=2 Hz, 5 Hz), 8.98 (1H, d, J=2 Hz), 11.7 (1H, br s).

EXAMPLE 122

To a solution of 1-hydroxy-2-(2,4-dimethoxyphenyl)-4-methyl-5-(3-pyridyl)imidazole (6.6 g) in N,N-dimethylformamide (130 ml) was added phosphorus trichloride (3.7 ml) under ice-cooling. The mixture was stirred for 2 hours at 5° to 10° C. The reaction mixture was poured into water, neutralized with aqueous sodium bicarbonate, and extracted with ethyl acetate. The extract was washed with water, dried, and evaporated. The residue was subjected to column chromatography on silica gel eluting with a mixture of chloroform and methanol (methanol 0% to 15%). The fractions were collected and evaporated to give 2-(2,4-dimethoxypheyl)-5-methyl-4-(3-pyridyl)imidazole (2.82 g).
mp: 164°–166° C.
IR (Nujol): 1615, 1590 cm$^{-1}$.
NMR (DMSO-d$_6$, δ): 2.47 (3H, s), 3.80 (3H, s), 3.93 (3H, s), 6.64 (1H, dd, J=2 Hz, 8 Hz), 6.68 (1H, d, J=2 Hz), 7.40 (1H, dd, J=5 Hz), 8 Hz), 7.9–8.2 (2H, m), 8.43 (1H, br d, J=5 Hz), 8.94 (1H, br s), 11.5 (1H, br s).

Other fractions were collected and evaporated to give 2-(2,4-dimethoxyphenyl)-5-hydroxymethyl-4-(3-pyridyl)imidazole (1.26 g).
mp: 192°–195° C.
IR (Nujol): 1615, 1595 cm$^{-1}$.
NMR (DMSO-d$_6$, δ): 3.83 (3H, s), 3.97 (3H, s), 4.70 (2H, br s), 5.26 (1H, br s), 6.66 (1H, dd, J=7 Hz, 2 Hz), 6.74 (1H, d, J=2 Hz), 7.24 (1H, dd, J=5 Hz, 8 Hz), 7.9–8.3 (2H, m), 8.47 (1H, dd, J=2 Hz, 5 Hz), 9.02 (1H, br s).

EXAMPLE 123

To a solution of 1-hydroxy-2-(2-methoxy-4-methylphenyl)-4-methyl-5-(3-pyridyl)imidazole (1.40 g) in N,N-dimethylformamide (28 ml), was added phosphorus trichloride (0.83 ml), and the mixture was stirred for 2 hours at ambient temperature. Then, the solution was poured into water (150 ml), and stirred for an hour at ambient temperature. After neutralized with aqueous sodium bicarbonate, resulting precipitates were collected by filtration. The precipitates were dried, dissolved in chloroform, and chromatographed on silica gel eluting with a mixture of chloroform and methanol. The fractions were collected, evaporated and triturated in diisopropyl ether to give 2-(2-methoxy-4-methylphenyl)-4-methyl-5-(3-pyridyl)imidazole (0.82 g)
mp: 125°–128° C.
IR (Nujol): 1615, 1590 cm$^{-1}$.

NMR (DMSO-d$_6$, δ): 2.37 (3H, s), 2.51 (3H, s), 3.95 (3H, s), 7.1–6.8 (2H, m), 7.42 (1H, dd, J=4 Hz, J=8 Hz), 8.00 (1H, d, J=7 Hz), 8.06 (1H, ddd, J=8 Hz, J=2 Hz, J=2 Hz), 8.44 (1H, dd, J=4 Hz, J=2 Hz), 8.94 (1H, d, J=2 Hz).

Mass (M/Z): 279 (M$^+$).

EXMPLE 124

To a solution of 1-hydroxy-2-(3-methoxy-4-methylthiophenyl)-4-methyl-5-(3-pyridyl)imidazole (0.98 g) in N,N-dimethylformamide (10 ml) was added triethyl phosphite (1.03 ml), and the mixture was stirred at 90° C. for 3 hours. Then the solution was poured into water (60 ml) and stirred at ambient temperature for an hour. The resulting precipitates were filtered, washed with water, and recrystallized from ethanol (6 ml) to give 2-(3-methoxy-4-methylthiophenyl)-4-methyl-5-(3-pyridyl)imidazole (0.58 g).

mp: 226°–228° C.

IR (Nujol): 1605, 1570 cm$^{-1}$.

NMR (DMSO-d$_6$, δ): 2.43 (3H, s), 2.51 (3H, s), 3.91 (3H, s), 7.18 (1H, d, J=9 Hz), 7.37 (1H, dd, J=8 Hz, J=4 Hz), 7.7–7.45 (2H, m), 8.03 (1H, ddd, J=8 Hz, J=2 Hz, J=2 Hz), 8.38 (1H, dd, J=4 Hz, J=2 Hz), 8.88 (1H, d, J=2 Hz), 12.4 (1H, br s).

Mass (M/Z): 311 (M$^+$).

The following compounds (Examples 125 to 183) were obtained according to a similar manner to that of Example 120, 121, 122, 123 or 124.

EXAMPLE 125

2-(3,4-Dimethoxyphenyl)-5-methyl-4-(2-pyridyl)imidazole.

mp: 96°–98° C.

IR (Nujol): 3300, 1720, 1590, 1500, 1260 cm$^{-1}$.

NMR (CDCl$_3$, δ): 2.62 (3H, s), 3.77 (3H, s), 3.86 (3H, s), 6.18 (1H, d, J=8 Hz), 6.9–7.1 (1H, m), 7.39 (1H, dd, J=2 Hz, 8 Hz), 7.44 (1H, s), 7.5–7.7 (2H, m), 8.40 (1H, d, J=5 Hz).

EXAMPLE 126

2-(3,4-Dimethoxyphenyl)-4-(2-pyridyl)imidazole.

mp: 80°–82° C.

IR (Nujol): 1680, 1590, 1490 cm$^{-1}$.

NMR (CDCl$_3$, δ): 3.83 (3H, s), 3.87 (3H, s), 6.81 (1H, d, J=8 Hz), 7.0–7.2 (1H, m), 7.36 (1H, dd, J=2 Hz, 8 Hz), 7.48 (1H, d, J=2 Hz), 7.60 (1H, s), 7.6–7.8 (2H, m), 8.42 (1H, d, J=6 Hz).

Mass (m/e): 281 (M$^+$).

EXAMPLE 127

2-(3,4-Dimethoxyphenyl)-5-methyl-4-(4-pyridyl)imidazole.

mp: 234°–236° C.

IR (Nujol): 1600 cm$^{-1}$.

NMR (CDCl$_3$-CD$_3$OD, δ): 2.50 (3H, s), 3.86 (3H, s), 3.91 (3H, s), 6.86 (1H, d, J=8 Hz), 7.7–7.3 (4H, m), 8.42 (2H, d, J=6 Hz).

EXAMPLE 128

2-(3,4-Dimethoxyphenyl)-5-ethyl-4-(4-pyridyl)imidazole.

mp: 181°–182° C. (dec.).

IR (Nujol): 1595, 1530, 1410 cm$^{-1}$.

NMR (CDCl$_3$, δ): 1.31 (3H, t, J=7.5 Hz), 2.85 (2H, q, J=7.5 Hz), 3.83 (6H, s), 6.77 (1H, d, J=9 Hz), 7.37 (1H, dd, J=2 Hz, 9 Hz), 7.49 (1H, d, J=2 Hz), 7.54 (4H, ABq, J=6 Hz).

Mass (m/e): 309 (M$^{30}$).

EXAMPLE 129

2-(2,4-Dimethoxyphenyl)-5-methyl-4-(2-pyridyl)imidazole.

mp: 118°–120° C.

IR (Nujol): 3260, 1610, 1580, 1490 cm$^{-1}$.

NMR (CDCl$_3$, δ): 2.64 (3H, s), 3.84 (3H, s), 4.01 (3H, s), 6.53 (1H, s), 6.57 (1H, dd, J=2 Hz, 9 Hz), 7.01 (1H, dd, J=6 Hz, 10 Hz), 7.5–7.8 (2H, m), 8.23 (1H, d, J=10 Hz), 8.50 (1H, d, J=6 Hz).

EXAMPLE 130

2-(3,4-Dimethoxyphenyl)-5-ethyl-4-(2-pyridylimidazole.

mp: 160°–163° C.

IR (Nujol): 1590, 1500, 1270, 1015 cm$^{-1}$.

NMR (CDCl$_3$, δ): 1.35 (3H, t, J=8 Hz), 2.99 (2H, t, J=8 Hz), 3.85 (6H, s), 6.80 (1H, d, J=9 Hz), 6.9–7.1 (1H, m), 7.33 (1H, dd, J=2 Hz, 9 Hz), 7.43 (1H, d, J=2 Hz), 7.5–7.7 (2H, m), 8.43 (1H, d, J=5 Hz).

EXAMPLE 131

2-(2,4-Dimethoxyphenyl)-5-methyl-4-(4-pyridyl)imidazole.

mp: 224°–226° C.

IR (Nujol): 1605 cm$^{-1}$.

NMR (DMSO-d$_6$, δ): 2.56 (3H, s), 3.85 (3H, s), 3.96 (3H, s), 6.6–6.8 (2H, m), 7.73 (2H, d, J=6 Hz), 8.07 (1H, d, J=9 Hz), 8.58 (2H, d, J=6 Hz), 11–12 (1H, br s).

EXAMPLE 132

2-(2,4-Dimethoxyphenyl)-5-ethyl-4-(4-pyridyl)imidazole.

mp: 212°–213° C.

IR (Nujol): 1595, 1530, 1505 cm$^{-1}$.

NMR (CDCl$_3$, δ): 1.36 (3H, t, J=8 Hz), 2.93 (2H, q, J=8 Hz), 3.83 (3H, s), 3.97 (3H, s), 6.51 (1H, d, J=2 Hz), 6.57 (1H, dd, J=2 Hz, 10 Hz), 7.52 (2H, dd, J=2 Hz), 8.23 (1H, d, J=10 Hz), 8.50 (1H, dd, J=2 Hz, 6 Hz).

Mass (m/e): 309 (M$^+$).

EXAMPLE 133

2-(2,4-Dimethoxyphenyl)-4-ethyl-5-(3-pyridyl)imidazole mp: 148°–151° C.

IR (Nujol): 1618, 1590, 1495 cm$^{-1}$.

NMR (DMSO-d$_6$, δ): 1.25 (3H, t, J=8 Hz), 2.85 (2H, q, J=8 Hz), 3.80 (3H, s), 3.91 (3H, s), 6.49–6.65 (2H, m), 6.63 (1H, s), 7.35 (1H, dd, J=8 Hz, 4 Hz), 7.82–8.01 (2H, m), 8.35 (1H, m), 8.79 (1H, br s).

EXAMPLE 134

2-(2,5-Dimethoxyphenyl)-5-methyl-4-(3-pyridyl)imidazole.

mp: 152°–154° C.

IR (Nujol): 1590 cm$^{-1}$.

NMR (DMSO-d$_6$, δ): 2.53 (3H, s), 3.78 (3H, s), 3.91 (3H, s), 6.88 (1H, dd, J=8 Hz, 2 Hz), 7.10 (1H, d, J=8 Hz), 7.40 (1H, dd, J=4 Hz, 8 Hz), 7.68 (1H, d, J=2 Hz), 8.07 (1H, ddd, J=8 Hz, 2 Hz), 8.44 (1H, br d, J=4 Hz), 8.97 (1H, br s).

EXAMPLE 135

2-(2,3-Dimethoxyphenyl)-5-methyl-4-(3-pyridyl)imidazole.

mp: 125°–127° C.

IR (Nujol): 1590, 1555 cm$^{-1}$.

NMR (DMSO-d$_6$, δ): 2.50 (3H, s), 3.77 (3H, s), 3.84 (3H, s), 6.96 (1H, dd, J=8 Hz, 2 Hz), 7.06 (1H, dd, J=8 Hz, 8 Hz), 7.32 (1H, dd, J=8 Hz, 4 Hz), 7.54 (1H, dd, J=2 Hz, 8 Hz), 7.97 (1H, ddd, J=2 Hz, 2 Hz, 8 Hz), 8.33 (1H, br d, J=4 Hz), 8.83 (1H, br s), 11.73 (1H, br s).

EXAMPLE 136

2-(2,3,4-Trimethoxyphenyl)-5-methyl-4-(3-pyridyl)imidazole.

mp: 144°–146° C. IR (Nujol): 1600 cm$^{-1}$.

NMR (DMSO-d$_6$, δ): 2.47 (3H, s), 3.78 (3H, s), 3.81 (3H, s), 3.83 (3H, s), 6.84 (1H, d, J=9 Hz), 7.32 (1H, dd, J=8 Hz, 4 Hz), 7.62 (1H, d, J=9 Hz), 7.96 (1H, br d, J=8 Hz), 8.32 (1H, br d, J=4 Hz), 8.82 (1H, br s), 11.62 (1H, br s).

EXAMPLE 137

2-(3,4,5-Trimethoxyphenyl)-5-methyl-4-(3-pyridyl)imidazole.

mp: 258°–260° C.

IR (Nujol): 1590 cm$^{-1}$.

NMR (CDCl$_3$-CD$_3$OD, δ): 2.45 (3H, s), 3.84 (3H, s), 3.90 (6H, s), 7.18 (2H, s), 7.33 (1H, dd, J=8 Hz, 5 Hz), 7.96 (1H, ddd, J=8 Hz, 2 Hz, 2 Hz), 8.34 (1H, br d, J=5 Hz), 8.72 (1H, br s).

EXAMPLE 138

2-(4-Chloro-2-methoxyphenyl)-5-methyl-4-(3-pyridyl)imidazole.

mp: 145°–147° C.

IR (Nujol): 1585, 1595 cm$^{-1}$.

NMR (DMSO-d$_6$, δ): 2.54 (3H, s), 4.01 (3H, s), 7.12 (1H, dd, J=8 Hz, 2 Hz), 7.25 (1H, d, J=2 Hz), 7.43 (1H, dd, J=8 Hz, 5 Hz), 8.08 (1H, ddd, J=8 Hz, 2 Hz, 2 Hz), 8.16 (1H, d, J=8 Hz), 8.47 (1H, dd, J=2 Hz, 5 Hz), 8.99 (1H, d, J=2 Hz), 11.75 (1H, br s).

EXAMPLE 139

2-(4-Acetamido-5-chloro-2-methoxyphenyl)-5-methyl-4-(3-pyridyl)imidazole.

mp: 239°–240° C.

IR (Nujol): 3400, 1680, 1590, 1520, 1490 cm$^{-1}$.

NMR (DMSO-d$_6$, δ): 2.14 (3H, s), 2.50 (3H, s), 3.91 (3H, s), 7.35 (1H, dd, J=5 Hz, 8 Hz), 7.63 (1H, s), 8.02 (1H, s) 8.02 (1H, dt, J=2 Hz, 8 Hz), 8.35 (1H, dd, J=2 Hz, 5 Hz), 8.82 (1H, d, J=2 Hz), 9.40 (1H, s), 11.63 (1H, s).

Mass (m/e): 356 (M+).

EXAMPLE 140

2-(4-Acetamido-2-methoxyphenyl)-5-methyl-4-(3-pyridyl)imidazole.

mp: 215°–218° C.

IR (Nujol): 1675, 1600 cm$^{-1}$.

NMR (DMSO-d$_6$, δ): 2.06 (3H, s), 2.49 (3H, s), 3.90 (3H, s), 7.14 (1H, dd, J=8 Hz, 2 Hz), 7.33 (1H, dd, J=8 Hz, 5 Hz), 7.48 (1H, d, J=2 Hz), 7.92 (1H, d, J=8 Hz), 7.96 (1H, ddd, J=8 Hz, 2 Hz, 2 Hz), 8.33 (1H, br d, J=5 Hz), 8.82 (1H, br s), 9.99 (1H, s), 11.45 (1H, br s).

EXAMPLE 141

2-Phenyl-5-methyl-4-(3-pyridyl)imidazole.

mp: 206°–208° C.

IR (Nujol): 1600, 1590, 1575 cm$^{-1}$.

NMR (DMSO-d$_6$, δ): 2.48 (3H, s), 7.2–7.6 (4H, m), 7.8–8.1 (3H, m), 8.35 (1H, br d, J=4 Hz), 8.83 (1H, br s), 12.39 (1H, br s).

EXAMPLE 142

2-(2-Methoxy-4-nitrophenyl)-4-methyl-5-(3-pyridyl)imidazole.

mp: 203°–207° C.

IR (Nujol): 1580 cm$^{-1}$.

NMR (DMSO-d$_6$, δ): 2.58 (3H, s), 4.11 (3H, s), 7.37 (1H, m), 7.75–8.14 (4H, m), 8.37 (1H, m), 8.88 (1H, br s), 11.93 (1H, br s).

EXAMPLE 143

2-(2-Methoxy-4-methylthiophenyl)-5-methyl-4-(3-pyridyl)imidazole.

mp: 153°–156° C.

IR (Nujol): 1600, 1580, 1565 cm$^{-1}$.

NMR (DMSO-d$_6$, δ): 2.48 (3H, s), 2.52 (3H, s), 3.94 (3H, s), 6.89 (1H, dd, J=8 Hz, J=2 Hz), 6.94 (1H, d, J=2 Hz), 7.34 (1H, dd, J=8 Hz, J=4 Hz), 7.96 (1H, d, J=8 Hz), 7.98 (1H, ddd, J=8 Hz, J=2 Hz, J=2 Hz), 8.34 (1H, dd, J=4 Hz, J=2 Hz), 8.84 (1H, d, J=2 Hz), 11.45 (1H, br s).

EXAMPLE 144

2-(2-Methoxy-4-methylthiophenyl)-5-hydroxymethyl-4-(3-pyridyl)imidazole mp: 199°–201° C.

IR (Nujol): 1605, 1590, 1575 cm$^{-1}$.

NMR (DMSO-d$_6$, δ): 2.52 (3H, s), 3.94 (3H, s), 4.61 (2H, d, J=4 Hz), 5.20 (1H, br t, J=4 Hz), 6.88 (1H, dd, J=8 Hz, 2 Hz), 6.93 (1H, d, J=2 Hz), 7.35 (1H, dd, J=8 Hz, J=4 Hz), 7.97 (1H, d, J=8 Hz), 8.06 (1H, ddd, J=8 Hz, 2 Hz, 2 Hz), 8.37 (1H, br d, J=4 Hz), 8.90 (1H, br s), 11.57 (1H, br s).

EXAMPLE 145

2-(4-Amino-5-chloro-2-methoxyphenyl)-5-methyl-4-(3-pyridyl)imidazole mp: 178°–180° C.

IR (Nujol): 3480, 3280, 3150, 1630, 1600, 1560 cm$^{-1}$.

NMR (DMSO-d$_6$, δ): 2.50 (3H, s), 3.87 (3H, s), 5.58 (2H, s), 6.52 (1H, s), 7.32 (1H, dd, J=5 Hz, 8 Hz), 7.80 (1H, s), 7.98 (1H, dt, J=2 Hz, 8 Hz), 8.34 (1H, dd, J=2 Hz, 5 Hz), 8.82 (1H, d, J=2 Hz), 11.30 (1H, br s).

Mass (m/e): 314 (M+).

EXAMPLE 146

2-(4-Amino-2-methoxyphenyl)-5-methyl-4-(3-pyridyl)imidazole.

mp: 95°–100° C.

IR (Nujol): 1615 cm$^{-1}$.

NMR (DMSO-d$_6$, δ): 2.45 (3H, s), 3.83 (3H, s), 5.32 (2H, br s), 6.18 (1H, dd, J=8 Hz, 2 Hz), 6.24 (1H, d, J=2 Hz), 7.30 (1H, dd, J=8 Hz, 4 Hz), 7.67 (1H, d, J=8 Hz), 7.94 (1H, ddd, J=8 Hz, 2 Hz, 2 Hz), 8.30 (1H, dd, J=4 Hz, 2 Hz), 8.80 (1H, d, J=2 Hz), 11.13 (1H, br s).

EXAMPLE 147

2-(2,6-Dimethoxyphenyl)-4-methyl-5-(3-pyridyl)imidazole.

mp: 185°–187° C.

IR (Nujol): 1608, 1590 cm$^{-1}$.

NMR (DMSO-d$_6$, δ): 2.44 (3H, s), 3.72 (6H, s), 6.74 (2H, d, J=8 Hz), 7.55–7.25 (2H, m), 7.98 (1H, ddd, J=8 Hz, J=2 Hz, J=2 Hz), 8.38 (1H, dd, J=5 Hz, J=2 Hz), 8.85 (1H, d, J=2 Hz), 11.9 (1H, br s).

Mass (M/Z): 295 (M+).

EXAMPLE 148

2-(3-Methoxy-4-methylthiophenyl)-4-methyl-5-(4-pyridyl)imidazole.
  mp: 283°–285° C.
  IR (Nujol): 1600 cm$^{-1}$.
  NMR (DMSO-d$_6$, δ): 2.43 (3H, s), 2.53 (3H, s), 3.93 (3H, s), 7.22 (1H, d, J=8 Hz), 7.8–7.4 (4H, m), 8.54 (2H, d, J=8 Hz), 12.50 (1H, br s).
  Mass (M/Z): 311 (M+).

EXAMPLE 149

2-(2-Methoxy-4-methylthiophenyl)-4-methyl-5-(4-pyridyl)imidazole.
  mp: 192°–194° C.
  IR (Nujol): 1606, 1565 cm$^{-1}$.
  NMR (DMSO-d$_6$, δ): 2.56 (3H, s), 2.58 (3H, s), 4.00 (3H, s), 6.99 (1H, dd, J=9 Hz, J=2 Hz), 7.04 (1H, d, J=2 Hz), 7.73 (2H, d, J=6 Hz), 8.09 (1H, d, J=9 Hz), 8.57 (2H, d, J=6 Hz), 11.55 (1H, br s).
  Mass (M/Z): 311 (M+).

EXAMPLE 150

4-Methyl-2-(2-nitrophenyl)-5-(3-pyridyl)imidazole.
  mp: 229°–230° C.
  IR (Nujol): 1613, 1601, 1578, 1539, 1497 cm$^{-1}$.
  NMR (DMSO-d$_6$, δ): 2.51 (3H, s), 7.40 (1H, dd, J=8 Hz, 5 Hz), 7.54–8.06 (5H, m), 8.45 (1H, dd, J=5 Hz, J=2 Hz), 8.87 (1H, d, J=2 Hz), 12.7 (1H, br s).
  Mass (M/Z): 280 (M+).

EXAMPLE 151

4-Methyl-2-(δ-tolyl)-5-(3-pyridyl)imidazole.
  mp: 129°–130° C.
  IR (Nujol): 1604, 1570, 1494 cm$^{-1}$.
  NMR (DMSO-d$_6$, δ): 2.57 (3H, s), 2.72 (3H, s), 7.3–7.9 (5H, m), 8.18 (1H, ddd, J=8 Hz, 2 Hz, 2 Hz), 8.52 (1H, dd, J=5 Hz, 2 Hz), 9.08 (1H, d, J=2 Hz).
  Mass (M/Z): 249 (M+).

EXAMPLE 152

2-(4-Chlorophenyl)-4-methyl-5-(3-pyridyl)imidazole.
  mp: 229°–231° C.
  IR (Nujol): 1600, 1574, 1492 cm$^{-1}$.
  NMR (DMSO-d$_6$, δ): 2.48 (3H, s), 7.32–7.58 (3H, m), 7.89–8.13 (3H, m), 8.43 (1H, dd, J=5 Hz, 2 Hz), 8.88 (1H, d, J=2 Hz)
  Mass (M/Z): 269 (M+).

EXAMPLE 153

2-[4-(N-Acetyl-N-methylamino)-5-chloro-2-methoxyphenyl]-4-methyl-5-(3-pyridyl)imidazole
  mp: 220°–221° C.
  IR (Nujol): 1672, 1599, 1563, 1525, 1490 cm$^{-1}$.
  NMR (DMSO-d$_6$, δ): 2.52 (3H, s), 2.79 (3H, s), 3.14 (3H, s), 4.01 (3H, s), 7.28–7.56 (2H, m), 7.95–8.26 (2H, m), 8.44 (1H, dd, J=5 Hz, 2 Hz), 8.91 (1H, d, J=2 Hz).
  Mass (M/Z): 370 (M+).

EXAMPLE 154

2-(2-Chlorophenyl)-4-methyl-5-(3-pyridyl)imidazole.
  mp: 108°–109° C.
  IR (Nujol): 1590, 1562, 1480 cm$^{-1}$.
  NMR (DMSO-d$_6$, δ): 2.51 (3H, s), 7.25–7.9 (5H, m), 8.09 (1H, ddd, J=8 Hz, 2 Hz, 2 Hz), 8.43 (1H, dd, J=5 Hz, 2 Hz), 8.92 (1H, d, J=2 Hz), 12.2 (1H, br s).
  Mass (M/Z): 269 (M+).

EXAMPLE 155

2-(3,4-Dichlorophenyl)-4-methyl-5-(3-pyridyl)imidazole.
  mp: 269° C.
  IR (Nujol): 1600, 1574 cm$^{-1}$.
  NMR (DMSO-d$_6$, δ): 2.51 (3H, s), 7.46 (1H, dd, J=8 Hz, 5 Hz), 7.71 (1H, d, J=8 Hz), 7.8–8.25 (3H, m), 8.45 (1H, d, J=5 Hz), 8.93 (1H, s), 12.68 (1H, br s)
  Mass (M/Z): 303 (M-1).

EXAMPLE 156

2-(4-Fluorophenyl)-4-methyl-5-(3-pyridyl)imidazole.
  mp: 123°–124° C.
  IR (Nujol): 1600, 1570, 1539, 1502 cm$^{-1}$.
  NMR (DMSO-d$_6$, δ): 2.52 (3H, s), 7.16–7.53 (3H, m), 7.87–8.19 (3H, m), 8.48 (1H, dd, J=5 Hz, 2 Hz), 8.97 (1H, d, J=2 Hz).
  Mass (M/Z): 253 (M+).

EXAMPLE 157

2-(3-Chlorophenyl)-4-methyl-5-(3-pyridyl)imidazole.
  mp: 242°–243° C.
  IR (Nujol): 1607, 1587, 1574, 1489 cm$^{-1}$.
  NMR (DMSO-d$_6$, δ): 2.52 (3H, s), 7.22–7.56 (3H, m), 7.79–8.21 (3H, m), 8.47 (1H, dd, J=5 Hz, 2 Hz), 8.95 (1H, s).
  Mass (M/Z): 269 (M+).

EXAMPLE 158

2-(2-Fluorophenyl)-4-methyl-5-(3-pyridyl)imidazole.
  mp: 194°–195° C.
  IR (Nujol): 1599, 1590, 1567, 1525, 1485 cm$^{-1}$.
  NMR (DMSO-d$_6$, δ): 2.60 (3H, s), 7.24–7.63 (4H, m), 7.95–8.36 (2H, m), 8.53 (1H, dd, J=5 Hz, 2 Hz), 9.08 (1H, d, J=2 Hz).
  Mass (M/Z): 253 (M+)

EXAMPLE 159

2-(2,4-Dichlorophenyl)-4-methyl-5-(3-pyridyl)imidazole.
  mp: 160°–161° C.
  IR (Nujol): 1590, 1569, 1556, 1484 cm$^{-1}$.
  NMR (DMSO-d$_6$, δ): 2.52 (3H, s), 7.38 (1H, dd, J=8 Hz, 5 Hz), 7.49 (1H, dd, J=8 Hz, 2 Hz), 7.69 (1H, d, J=2 Hz), 7.83 (1H, d, J=8 Hz), 8.04 (1H, ddd, J=8 Hz, 2 Hz, 2 Hz), 8.43 (1H, d, J=5 Hz), 8.91 (1H, s), 12.46 (1H, br s).
  Mass (M/Z): 303 (M-1).

EXAMPLE 160

2-(5-Chloro-2,4-dimethoxyphenyl)-4-methyl-5-(3-pyridyl)imidazole.
  mp: 241°–244° C.
  IR (Nujol): 1610, 1590, 1565 cm$^{-1}$.
  NMR (CDCl$_3$-CD$_3$OD, δ): 2.50 (3H, s), 3.86 (3H, s), 3.94 (3H, s), 6.61 (1H, s), 7.38 (1H, dd, J=8 Hz, J=4 Hz), 8.2–7.8 (2H, m), 8.36 (1H, br d, J=4 Hz), 8.74 (1H, br s).
  Mass (M/Z): 329 (M+).

EXAMPLE 161

2-(5-Chloro-2-methoxy-4-methylphenyl)-4-methyl-5-(3-pyridyl)imidazole.
  mp: 185°–187° C.
  IR (Nujol): 1600, 1580, 1560 cm$^{-1}$.
  NMR (DMSO-d$_6$, δ): 2.37 (3H, s), 2.52 (3H, s), 3.94 (3H, s), 7.13 (1H, s), 7.36 (1H, dd, J=8 Hz, J=4 Hz), 8.00 (1H, s), 8.03 (1H, ddd, J=2 Hz, J=2 Hz, J=8 Hz), 8.37 (1H, dd, J=2 Hz, J=4 Hz), 8.87 (1H, d, J=2 Hz), 11.63 (1H, br s).
Mass (M/Z): 313 (M+).

EXAMPLE 162

2-(4-Methoxyphenyl)-4-methyl-5-(3-pyridyl)imidazole.
mp: 199°–201° C.
IR (Nujol): 1615, 1600 cm$^{-1}$.
NMR (DMSO-d$_6$, δ): 2.51 (3H, s), 3.83 (3H, s), 7.05 (2H, d, J=9 Hz), 7.42 (1H, dd, J=5 Hz, J=8 Hz), 7.8–8.2 (3H, m), 8.45 (1H, dd, J=5 Hz, J=2 Hz), 8.94 (1H, d, J=2 Hz), 12.1 (1H, br s).
Mass (M/Z): 265 (M+).

EXAMPLE 163

4-Methyl-5-(3-pyridyl)-2-(2,4,6-trimethoxyphenyl)imidazole.
mp: 65°–75° C.
IR (Nujol): 1610, 1590 cm$^{-1}$.
NMR (DMSO-d$_6$, δ): 2.42 (3H, s), 3.69 (3H, s), 3.83 (3H, s), 6.28 (2H, s), 7.33 (1H, dd, J=8 Hz, J=4 Hz), 7.93 (1H, br d J=8 Hz), 8.32 (1H, br d, J=4 Hz), 8.80 (1H, br s).
Mass (M/Z): 325 (M+).

EXAMPLE 164

4-Methyl-5-(3-pyridyl)-2-(2,4,5-trimethoxyphenyl)imidazole.
mp: 189°–191° C.
IR (Nujol): 1615, 1600 cm$^{-1}$.
NMR (DMSO-d$_6$, δ): 2.47 (3H, s), 3.76 (3H, s), 3.83 (3H, s), 3.93 (3H, s), 6.74 (1H, s), 7.35 (1H, dd, J=8 Hz, J=4 Hz), 7.60 (1H, s), 7.99 (1H, ddd, J=2 Hz, 2 Hz, 8 Hz), 8.46 (1H, dd, J=2 Hz, J=4 Hz), 8.85 (1H, d, J=2 Hz).
Mass (M/Z): 325 (M+).

EXAMPLE 165

2-(4-Benzyloxy-2-methoxyphenyl)-4-methyl-5-(3-pyridyl)imidazole.
mp: 160°–162° C.
IR (Nujol): 1615, 1590 cm$^{-1}$.
NMR (DMSO-d$_6$, δ): 2.48 (3H, s), 3.92 (3H, s), 5.14 (2H, s), 6.69 (1H, dd, J=8 Hz, J=2 Hz), 6.74 (1H, d, J=2 Hz), 7.6–7.2 (6H, m), 8.1–7.8 (2H, m), 8.36 (1H, br d, J=4 Hz), 8.86 (1H, br s).
Mass (M/Z): 371 (M+).

EXAMPLE 166

2-(4-Ethoxy-2-methoxyphenyl)-4-methyl-5-(3-pyridyl)imidazole.
mp: 151°–153° C.
IR (Nujol): 1615, 1590 cm$^{-1}$.
NMR (DMSO-d$_6$, δ): 1.36 (3H, t, J=7 Hz), 2.53 (3H, s), 3.94 (3H, s), 4.10 (2H, q, J=7 Hz), 6.63 (1H, dd, J=2 Hz, J=7 Hz), 6.68 (1H, d, J=2 Hz), 7.41 (1H, dd, J=8 Hz, J=4 Hz), 7.8–8.3 (2H, m), 8.42 (1H, d, J=4 Hz), 8.95 (1H, br s), 11.50 (1H, br s).
Mass (M/Z): 309 (M+).

EXAMPLE 167

2-(5-Chloro-2-methoxyphenyl)-4-methyl-5-(3-pyridyl)imidazole.
mp: 193°–195° C.
IR (Nujol): 1600, 1586, 1565, 1619 cm$^{-1}$.
NMR (DMSO-d$_6$, δ): 2.53 (3H, s), 3.95 (3H, s), 7.11 (1H, d, J=8 Hz), 7.21–7.48 (2H, m), 7.89–8.13 (2H, m), 8.39 (1H, d, J=5 Hz), 8.88 (1H, s), 11.72 (1H, br s).
Mass (M/Z): 298 (M+).

EXAMPLE 168

2-(4-Hydroxy-3-methoxyphenyl)-4-methyl-5-(3-pyridyl)imidazole.
mp: 278°–279° C.
IR (Nujol): 1609, 1575, 1508, 1490 cm$^{-1}$.
NMR (DMSO-d$_6$, δ): 2.43 (3H, s), 3.83 (3H, s), 6.79 (1H, d, J=8 Hz), 7.2–7.55 (3H, m), 7.97 (1H, d, J=8 Hz), 8.35 (1H, s), 8.83 (1H, s), 9.13 (1H, s).
MASS (M/Z): 281 (M+).

EXAMPLE 169

2-(3-Hydroxy-4-methoxyphenyl)-4-methyl-5-(3-pyridyl)imidazole.
mp: 267°–269° C.
IR (Nujol): 1595, 1574, 1505 cm$^{-1}$.
NMR (DMSO-d$_6$, δ): 2.45 (3H, s), 3.82 (3H, s), 7.00 (1H, d, J=8 Hz), 7.26–7.56 (3H, m), 8.05 (1H, ddd, J=8 Hz, 2 Hz, 2 Hz), 8.40 (1H, dd, J=5 Hz, 2 Hz), 8.86 (1H, d, J=2 Hz), 9.08 (1H, s), 12.10 (1H, br s).
MASS (M/Z): 281 (M+).

EXAMPLE 170

2-(3-Chloro-4,5-dimethoxyphenyl)-4-methyl-5-(3-pyridyl)imidazole.
mp: 215°–216° C.
IR (Nujol): 1573, 1497 cm$^{-1}$.
NMR (DMSO-d$_6$, δ): 2.50 (3H, s), 3.90 (3H, s), 3.96 (3H, s), 7.42 (1H, dd, J=8 Hz, 5 Hz), 7.67 (2H, s), 8.10 (1H, ddd, J=8 Hz, 2 Hz, 2 Hz), 8.47 (1H, dd, J=5 Hz, 2 Hz), 8.93 (1H, d, J=2 Hz).
Mass (M/Z): 329 (M+).

EXAMPLE 171

2-(3-Chloro-4-hydroxy-5-methoxyphenyl)-4-methyl-5-(3-pyridyl)imidazole.
mp: 251°–253° C.
IR (Nujol): 1575, 1504 cm$^{-1}$.
NMR (DMSO-d$_6$, δ): 2.47 (3H, s), 3.93 (3H, s), 7.42 (1H, br s), 7.54 (1H, s), 7.57 (1H, s), 8.05 (1H, d, J=8 Hz), 8.42 (1H, s), 8.90 (1H, s), 9.62 (1H, s), 12.33 (1H, br s).
Mass (M/Z): 315 (M+).

EXAMPLE 172

4-Methyl-2-(2-methoxy-5-nitrophenyl)-5-(3-pyridyl)imidazole.
mp: 220°–223° C.
IR (Nujol): 1593, 1534, 1508, 1490 cm$^{-1}$.
NMR (DMSO-d$_6$, δ): 2.52 (3H, s), 4.07 (3H, s), 7.18–7.46 (2H, m), 7.85–8.12 (2H, m), 8.47 (1H, d, J=5 Hz), 8.77–8.91 (2H, m), 11.86 (1H, br s).
Mass (M/Z): 310 (M+).

EXAMPLE 173

4-Methyl-2-(2-methoxy-3-nitrophenyl)-5-(3-pyridyl)imidazole.
mp: 145°–150° C.
IR (Nujol): 1600, 1566, 1535 cm$^{-1}$.
NMR (DMSO-d$_6$, δ): 2.53 (3H, s), 3.78 (3H, s), 7.2–7.5 (2H, m), 7.83 (1H, dd, J=8 Hz, 2 Hz), 8.02 (1H, d, J=8 Hz), 8.18 (1H, dd, J=8 Hz, 2 Hz), 8.36 (1H, d, J=5 Hz), 8.87 (1H, s), 12.24 (1H, br s).
Mass (M/Z): 310 (M+).

EXAMPLE 174

2-(2-Methoxy-4-methylsulfinylphenyl)-4-methyl-5-(3-pyridyl)imidazole
IR (Nujol): 1660, 1600 cm$^{-1}$.

EXAMPLE 175

2-(2-Methoxy-4-methylsulfonylphenyl)-4-methyl-5-(3-pyridyl)imidazole.
mp: 115°–118° C.
IR (Nujol): 1600, 1590 cm$^{-1}$.

EXAMPLE 176

2-(2-Aminophenyl)-4-methyl-5-(3-pyridyl)imidazole.
mp: 221°–222° C.
IR (Nujol): 3450, 1618, 1602, 1573, 1600 cm$^1$.

EXAMPLE 177

2-(5-Amino-2-methoxyphenyl)-4-methyl-5-(3-pyridyl)imidazole.
mp: 172°–173° C.
IR (Nujol): 3430, 1598, 1569, 1530, 1495 cm$^{-1}$.

EXAMPLE 178

4-Methyl-2-(4-methylamino-2-methylphenyl)-5-(3-pyridyl)imidazole.
mp: 54°–56° C.
IR (Nujol): 1612, 1580, 1560 cm$^{-1}$.

EXAMPLE 179

2-(2-Acetamidophenyl)-4-methyl-5-(3-pyridyl)imidazole.
mp: 270°–271° C.
IR (Nujol): 1700, 1620, 1598, 1580, 1545, 1495 cm$^{-1}$.

EXAMPLE 180

4-Methyl-2-[2-(3-methylureido)phenyl]-5-(3-pyridyl)imidazole.
mp: 230°–231° C.
IR (Nujol): 3270, 1684, 1658, 1618, 1589, 1493 cm$^{-1}$.

EXAMPLE 181

2-(4-Hydroxy-2-methoxyphenyl)-4-methyl-5-(3-pyridyl)imidazole.
mp: 237°–240° C.
IR (Nujol): 1610 cm$^{-1}$.

EXAMPLE 182

2-(5-Bromo-2,4-dimethoxyphenyl)-4-methyl-5-(3-pyridyl)imidazole.
mp: 246°–248° C.
IR (Nujol): 1600, 1580 cm$^{=1}$.

EXAMPLE 183

2-(5-Chloro-4-methylamino-2-methoxyphenyl)-4-methyl-5-(3-pyridyl)imidazole.
mp: 205°–206° C.
IR (Nujol): 1616, 1570, 1546, 1498 cm$^{-1}$.

EXAMPLE 184

To a solution of 1-hydroxy-2-(3,4-dimethoxyphenyl)-4-ethyl-5-(3-pyridyl)imidazole (1.86 g) in N,N-dimethylformamide (38 ml) was added phosphorus trichloride (0.10 ml) under ice-cooling. The mixture was stirred for 2 hours at 5° to 10° C. The reaction mixture was poured into water, neutralized with aqueous sodium bicarbonate, and extracted with ethyl acetate. The extract was washed with water, dried, and evaporated. The residue was subjected to column chromatography on silica gel eluting with a mixture of chloroform and methanol (methanol 1% to 5%). The fractions were collected and evaporated to give 2-(3,4-dimethoxyphenyl)-4-ethyl-5-(3-pyridyl)imidazole (0.89 g), which was diluted with methanol (8 ml). 1.2 Equivalent of hydrogen chloride gas was bubbled thereinto and diethyl ether was added to the mixture under cooling. The precipitate was collected and dried to give 2-(3,4-dimethoxyphenyl)-4-ethyl-5-(3-pyridyl)imidazole hydrochloride (0.43 g).
mp: 245°–248° C.
IR (Nujol): 1650, 1605, 1515 cm$^{-1}$.
NMR (DMSO-d$_6$, δ): 1.33 (3H, t, J=8 Hz), 2.76 (2H, q, J=8 Hz), 3.71 (3H, s), 3.81 (3H, s), 6.82 (1H, d, J=8 Hz), 7.16 (1H, s), 7.10–7.30 (1H, m), 7.72 (1H, dd, J=8 Hz, 4 Hz), 8.15 (1H, d, J=8 Hz), 8.45–8.70 (2H, br s).

EXAMPLE 185

To a solution of 2-(2,4-dimethoxyphenyl)-5-methyl-4-(3-pyridyl)imidazole (0.80 g) in N,N-dimethylformamide (12 ml) was added sodium hydride (0.13 g, 60% suspension in oil), and the mixture was stirred for 10 minutes. Then methyl iodide (0.34 ml) was added thereto, and the reaction was stirred at ambient temperature for 5 hours. The solution was poured into water (100 ml), and extracted with ethyl acetate. The extract was washed with water, dried over sodium sulfate, and chromatographed on silica gel (25 g) eluting with chloroform. The fractions were collected and evaporated, and the residue was triturated with a mixture of ethyl acetate and diisopropyl ether (1:1 V/V) to give 2-(2,4-dimethoxyphenyl)-1,5-dimethyl-4-(3-pyridyl)imidazole (70 mg).
mp: 129°–131° C.
IR (Nujol): 1615, 1595, 1580 cm$^{-1}$.
NMR (DMSO-d$_6$, δ): 2.40 (3H, s), 3.30 (3H, s), 3.76 (3H, s), 3.80 (3H, s), 6.7–6.4 (2H, m), 7.20 (1H, d, J=8 Hz), 7.31 (1H, dd, J=4 Hz, 8 Hz), 7.89 (1H, br d, J=8 Hz), 8.32 (1H, br d, J=4 Hz), 8.74 (1H, br s).

EXAMPLE 186

A solution of 2-(2-Aminophenyl)-4-methyl-5-(3-pyridyl)imidazole (0.7 g) and 2-methylthio-2-imidazoline hydriodide (1.23 g) in N,N-dimethylformamide (10 ml) was stirred at 100° C. for 24 hours. The resulting precipitate was collected by filtration, washed with N,N-dimethylformamide and ethylacetate, successively. To a solution of the residue in ethanol (10 ml) was added a solution of 20% hydrogen chloride in ethanol (2 ml) at ambient temperature, and was evaporated under reduced pressure. The precipitate was triturated in ethanol and diethyl ether to give 2-(2-aminophenyl)-1,5-dimethyl-4-(3-pyridyl)imidazole dihydrochloride (0.13 g).
mp: 285°–286° C.
IR (Nujol): 1587, 1512 cm$^{-1}$.
NMR (D$_2$O, δ): 2.59 (3H, s), 4.48 (3H, s), 7.10–7.68 (4H, m), 8.05 (1H, dd, J=8 Hz, 6 Hz), 8.53–8.76 (2H, m), 8.99 (1H, s)
Mass (M/Z): 264 (M$^+$, free).

EXAMPLE 187

A solution of 2-(4-acetamido-5-chloro-2-methoxyphenyl)-5-methyl-4-(3-pyridyl)imidazole (1.0 g) in 10% hydrochloric acid (30 ml) was stirred at 80° to 85° C. for 4 hours. The reaction mixture was poured into water (100 ml) and washed with ethyl acetate. The solution was adjusted to pH 8.0 with 20% potassium carbonate and extracted with ethyl acetate. The extract was washed with brine and dried over magnesium sulfate. The solvent was evaporated in vacuo and the residue was crystallized from a mixture of ethyl acetate and diethyl ether to give 2-(4-amino-5-chloro-2-methoxyphenyl)-5-methyl-4-(3-pyridyl)imidazole (0.63 g).

mp: 178°–180° C.

IR (Nujol): 3480, 3280, 3150, 1630, 1600, 1560 cm$^{-1}$.

NMR (DMSO-$d_6$, δ): 2.50 (3H, s), 3.87 (3H, s), 5.58 (2H, s), 6.52 (1H, s), 7.32 (1H, dd, J=5 Hz, 8 Hz), 7.80 (1H, s), 7.98 (1H, dt, J=2 Hz, 8 Hz), 8.34 (1H, dd, J=2 Hz, 5 Hz), 8.82 (1H, d, J=2 Hz), 11.30 (1H, br s).

Mass (m/e): 314 (M+).

EXAMPLE 188

A solution of 2-(4-acetamido-2-methoxyphenyl)-5-methyl-4-(3-pyridyl)imidazole (0.55 g) in 1N-hydrochloric acid (25 ml) was refluxed for 5.5 hours, and cooled. After neutralized with aqueous sodium bicarbonate, the mixture was extracted with chloroform. The extract was dried over sodium sulfate, evaporated, and the residue was triturated with a mixture of methanol and diisopropyl ether to give 2-(4-amino-2-methoxyphenyl)-5-methyl-4-(3-pyridyl)imidazole (0.24 g).

mp: 95°–100° C.

IR (Nujol): 1615 cm$^{-1}$.

NMR (DMSO-$d_6$, δ): 2.45 (3H, s), 3.83 (3H, s), 5.32 (2H, br s), 6.18 (1H, dd, J=8 Hz, 2 Hz), 6.24 (1H, d, J=2 Hz), 7.30 (1H, dd, J=8 Hz, 4 Hz), 7.67 (1H, d, J=8 Hz), 7.94 (1H, ddd, J=8 Hz, 2 Hz, 2Hz), 8.30 (1H, dd, J=4 Hz, 2 Hz), 8.80 (1H, d, J=2 Hz), 11.13 (1H, br s).

EXAMPLE 189

A solution of 2-[4-(N-acetyl-N-methylamino)-5-chloro-2-methoxyphenyl]-4-methyl-5-(3-pyridyl)imidazole (0.70 g) and conc. hydrochloric acid (7 ml) in a mixture of water (7 ml) and ethanol (7 ml) was refluxed for 7 hours with stirring. After allowed to cool to ambient temperature, the mixture was evaporated under reduced pressure. The resulting oil was poured into water (20 ml). After neutrallized with aqueous potassium bicarbonate the mixture was extracted with ethyl acetate. The organic layer was washed with brine and dried over magnesium sulfate. The solvent was distilled off to give 2-(5-chloro-4-methylamino-2-methoxyphenyl)-4-methyl-5-(3-pyridyl)imidazole (0.58 g).

mp: 205°–206° C.

IR (Nujol): 1616, 1570, 1546, 498 cm$^{-1}$.

NMR (DMSO-$d_6$, δ): 2.51 (3H, s), 2.87 (3H, d, J=6 Hz), 3.97 (3H, s), 5.77 (1H, d, J=6 Hz), 6.32 (1H, s), 7.39 (1H, dd, J=8 Hz, 5 Hz), 7.92 (1H, s), 8.07 (1H, ddd, J=8 Hz, 2 Hz, 2 Hz), 8.40 (1H, d, J=5 Hz), 8.92 (1H, s), 11.38 (1H, br s).

EXAMPLE 190

To a solution of 2-(2-methoxy-5-methylthiophenyl)-4-methyl-5-(3-pyridyl)imidazole (1.0 g) in chloroform (50 ml) and ethanol (25 ml), was added a solution of m-chloroperbenzoic acid (0.53 g, 80% pure) in chloroform (5.3 ml) at −30° to −40° C. The mixture was stirred at the same temperature for 4 hours, and then warmed to ambient temperature. The reaction mixture was diluted with chloroform (100 ml) and washed with aqueous sodium bicarbonate and brine successively. After dried over sodium sulfate, the mixture was chromatographed on silica gel eluting with a mixture of chloroform and methanol to give 2-(2-methoxy-4-methylsulfinylphenyl)-4-methyl-5-(3-pyridyl)imidazole (0.82 g).

IR (Nujol): 1660, 1600 cm$^{-1}$.

NMR (CDCl$_3$, δ): 2.48 (3H, s), 2.72 (3H, s), 3.98 (3H, s), 7.16 (1H, dd, J=8 Hz, J=2 Hz), 7.25 (1H, dd, J=8 Hz, J=5 Hz), 7.33 (1H, d, J=2 Hz), 7.98 (1H, br, d, J=8 Hz), 8.35 (1H, d, J=8 Hz), 8.37 (1H, dd, J=2 Hz, J=5 Hz), 8.84 (1H, br s), 10.68 (1H, br s).

EXAMPLE 191

To a solution of 2-(2-methoxy-4-methylthiophenyl)-4-methyl-5-(3-pyridyl)imidazole (0.93 g) in acetic acid (10 ml) was added aqueous potassium permanganate (0.80 g in 15 ml) at ambient temperature, and the mixture was stirred at ambient temperature for 3 hours. After neutralized with aqueous sodium bicarbonate, the mixture was extracted with chloroform. The organic layer was washed with water, dried over sodium sulfate, and concentrated. The residue was chromatographed on silica gel eluting with a mixture of chloroform and methanol to give 2-(2-methoxy-4-methylsulfonylphenyl)-4-methyl-5-(3-pyridyl)imidazole (0.16 g).

mp: 115°–118° C.

IR (Nujol): 1600, 1590 cm$^{-1}$.

NMR (DMSO-$d_6$, δ): 2.53 (3H, s), 3.25 (3H, s), 4.05 (3H, s), 7.7–7.2 (3H, m), 7.8–8.5 (3H, m), 8.85 (1H, br s), 11.85 (1H, br s).

Mass (M/Z): 343 (M+).

EXAMPLE 192

A mixture of 4-methyl-2-(2-nitrophenyl)-5-(3-pyridyl)imidazole (4.99 g) and 10% palladium on carbon (1.0 g) in a mixture of tetrahydrofuran (150 ml) and methanol (150 ml) was hydrogenated at ambient temperature under atmospheric pressure of hydrogen gas. After removal of the catalyst by filtration, the filtrate was evaporated under reduced pressure. The residue was recrystallized from ethanol to give 2-(2-aminophenyl)-4-methyl-5-(3-pyridyl)imidazole (4.22 g).

mp: 221°–222° C.

IR (Nujol): 3450, 1618, 1602, 1573, 1600 cm$^{-1}$.

NMR (DMSO-$d_6$, δ): 2.52 (3H, s), 6.54–7.23 (3H, m), 7.45 (1H, dd, J=8 Hz, 5 Hz), 7.64 (1H, d, J=8 Hz), 8.10 (1H, ddd, J=8 Hz, 2 Hz, 2 Hz), 8.48 (1H, dd, J=5 Hz, 2 Hz), 8.95 (1H, d, J=2 Hz).

Mass (M/Z): 250 (M+).

EXAMPLE 193

2-(5-Amino-2-methoxyphenyl)-4-methyl-5-(3-pyridyl)imidazole was obtained according to a similar manner to that of Example 192.

mp: 172°–173° C.

IR (Nujol): 3430, 1598, 1569, 1530, 1495 cm$^{-1}$.

NMR (DMSO-$d_6$, δ): 2.49 (3H, s), 3.82 (3H, s), 6.53 (1H, dd, J=8 Hz, 2 Hz), 6.83 (1H, d, J=8 Hz), 7.22–7.48 (2H, m), 7.98 (1H, ddd, J=8 Hz, 2 Hz, 2 Hz), 8.36 (1H, dd, J=5 Hz, 2 Hz), 8.87 (1H, d, J=2 Hz).

Mass (M/Z): 280 (M+).

EXAMPLE 194

A mixture of 2-(5-Chloro-4-methylamino-2-methoxyphenyl)-4-methyl-5-(3-pyridyl)imidazole (0.50 g) and 10% palladium on carbon (7.5 g) in a mixture of triethylamine (0.64 ml) and methanol (20 ml) was hydrogenated at ambient temperature under atmospheric pressure of hydrogen gas. After removal of the insoluble substance by filtration, the filtrate was evaporated under reduced pressure. The residue was triturated in diisopropyl ether to give 4-methyl-2-(4-methylamino-2-methoxyphenyl)-5-(3-pyridyl)imidazole (0.10 g).

mp: 54°–56° C.

IR (Nujol): 1612, 1580, 1560 cm$^{-1}$.

NMR (DMSO-d$_6$, δ): 2.48 (3H, s), 2.75 (3H, d, J=6 Hz), 3.92 (3H, s), 5.94 (1H, d, J=6 Hz), 6.15–6.35 (2H, m), 7.38 (1H, dd, J=8 Hz, 5 Hz), 7.81 (1H, d, J=8 Hz), 8.02 (1H, d, J=8 Hz), 8.37 (1H, d, J=5 Hz), 8.88 (1H, s), 11.22 (1H, br s).

Mass (M/Z): 294 (M+).

EXAMPLE 195

A solution of 2-(2-aminophenyl)-4-methyl-5-(3-pyridyl)imidazole (0.5 g) and acetic anhydride (0.38 ml) in acetic acid (5 ml) was stirred at ambient temperature for 1.5 hours. The resulting precipitate was collected by filtration, and recrystallized from ethanol to give 2-(2-acetamidophenyl)-4-methyl-5-(3-pyridyl)imidazole (0.55 g).

mp: 270°–271° C.

IR (Nujol): 1700, 1620, 1598, 1580, 1545, 1495 cm$^{-1}$.

NMR (DMSO-d$_6$, δ): 2.21 (3H, s), 2.52 (3H, s), 7.0–7.6 (3H, m), 7.85 (1H, s), 8.10 (1H, ddd, J=8 Hz, 2 Hz, 2 Hz), 8.4–8.75 (2H, m), 8.97 (1H, d, J=2 Hz).

Mass (M/Z): 292 (M+).

EXAMPLE 196

A solution of 2-(2-aminophenyl)-4-methyl-5-(2-pyridyl)imidazole (0.5 g) and methylisocyanate (0.15 ml) in a mixture of tetrahydrofuran (5 ml) and methanol (2 ml) was stirred at ambient temperature for 5 hours. The resulting precipitate was collected by filtration, washed with a mixture of ethanol and chloroform and dried in vacuo to give 4-methyl-2-[2-(3-methylureido)-phenyl]-5-(3-pyridyl)imidazole (0.51 g).

mp: 230°–231° C.

IR (Nujol): 3270, 1684, 1658, 1618, 1589, 1493 cm$^{-1}$.

NMR (D$_2$O-DCl, δ): 2.62 (3H, s), 2.70 (3H, s), 7.38–7.95 (4H, m), 8.38 (1H, dd, J=8 Hz, 5 Hz), 8.8–9.1 (2H, m), 9.21 (1H, d, J=2 Hz).

Mass (M/Z): 307 (M+).

EXAMPLE 197

To a solution of 2-(4-benzyloxy-2-methoxyphenyl)-4-methyl-5-(3-pyridyl)imidazole (1.18 g) in methanol (12 ml) and tetrahydrofuran (6 ml) was added 10% palladium on carbon (wet ca. 50%, 0.30 g), and the mixture was stirred for 7 hours at ambient temperature under atmospheric pressure of hydrogen gas. The mixture was filtered, and the filtrate was evaporated. The residue was dissolved in methanol (20 ml), and hydrogenated again on palladium on carbon (wet, 0.50 g) for 5 hours. After the filtration, the filtrate was evaporated, and the residue was triturated in a mixture of diisopropyl ether and isopropanol (1:1 V/V) to give 2-(4-hydroxy-2-methoxyphenyl)-4-methyl-5-(3-pyridyl)imidazole (0.25 g).

mp: 237°–240° C.

IR (Nujol): 1610 cm$^{-1}$.

NMR (DMSO-d$_6$, δ): 2.47 (3H, s), 3.89 (3H, s), 6.53 (1H, dd, J=8 Hz, J=2 Hz), 6.60 (1H, d, J=2 Hz), 7.46 (1H, dd, J=8 Hz, J=5 Hz), 7.89 (1H, d, J=8 Hz), 8.07 (1H, ddd, J=8 Hz, J=2 Hz, J=2 Hz), 8.51 (1H, dd, J=5 Hz, J=2 Hz), 8.92 (1H, d, J=2 Hz), 10.0 (1H, br s).

Mass (M/Z): 281 (M+).

EXAMPLE 198

To a solution of 2-(2,4-dimethoxyphenyl)-4-methyl-5-(3-pyridyl)imidazole (1.0 g) in acetic acid (10 ml) were added a solution of hydrogen bromide in acetic acid (28%, 0.2 ml) and pyridinium hydrobromide perbromide (1.49 g), and was stirred at ambient temperature for 19 hours. Then the mixture was poured into ice-water (100 ml), adjusted to pH 4.8 with 8N sodium hydroxide, and extracted with chloroform. The organic layer was washed by aqueous sodium bicarbonate and evaporated, and the residue was triturated in diisopropyl ether to give 2-(5-bromo-2,4-dimethoxyphenyl)-4-methyl-5-(3-pyridyl)imidazole (0.92 g).

mp: 246°–248° C.

IR (Nujol): 1600, 1580 cm$^{-1}$.

NMR (DMSO-d$_6$, δ): 2.52 (3H, s), 2.96 (3H, s), 3.96 (3H, s), 4.03 (3H, s), 6.89 (1H, s), 7.43 (1H, dd, J=8 Hz, J=5 Hz), 8.11 (1H, ddd, J=8 Hz, J=2 Hz, J=2 Hz), 8.24 (1H, s), 8.47 (1H, dd, J=2 Hz, J=5 Hz), 8.97 (1H, d, J=2 Hz), 11.6 (1H, br s).

Mass (M/Z): 373 (M+).

EXAMPLE 199

To a solution of 2-(2,4-dimethoxyphenyl)-4-methyl-5-(3-pyridyl)imidazole (0.9 g) in ethanol (20 ml) was added conc. hydrochloric acid (0.6 ml), and the mixture was evaporated. The resulting syrup was triturated in ethanol to give 2-(2,4-dimethoxyphenyl)-4-methyl-5-(3-pyridyl)imidazole dihydrochloride (1.02 g).

mp: 247°–248° C.

IR (Nujol): 1615, 1580 cm$^{-1}$.

NMR (DMSO-d$_6$, δ): 2.56 (3H, s), 3.91 (3H, s), 4.01 (3H, s), 6.78 (1H, dd, J=7 Hz, J=2 Hz), 6.86 (1H, d, J=2 Hz), 8.3–7.8 (2H, m), 8.65 (1H, ddd, J=8 Hz, J=2 Hz, J=2 Hz), 8.87 (1H, dd, J=5 Hz, J=2 Hz), 9.20 (1H, d, J=2 Hz).

EXAMPLE 200

2-(2-Methoxy-4-methylsulfinylphenyl)-4-methyl-5-(3-pyridyl)imidazole dihydrochloride was obtained according to a similar manner to that of Example 199.

mp: 212°–215° C.

IR (Nujol): 1640, 1600, 1580 cm$^{-1}$.

NMR (DMSO-d$_6$, δ): 2.55 (3H, s), 2.84 (3H, s), 4.03 (3H, s), 7.41 (1H, dd, J=8 Hz, J=2 Hz), 7.49 (1H, d, J=2 Hz), 7.66 (1H, dd, J=5 Hz, J=8 Hz), 8.19 (1H, d, J=8 Hz), 8.28 (1H, ddd, J=2 Hz, J=2 Hz, J=8 Hz), 8.62 (1H, dd, J=2 Hz, J=5 Hz), 8.91 (1H, d, J=2 Hz).

Mass (M/Z)=327 (M+, Free).

EXAMPLE 201

2-[4-(Dimethylamino)-2-methoxyphenyl]-4-methyl-5-(3-pyridyl)imidazole was obtained according to a similar manner to that of Example 124.

And then its dihydrochloride was obtained according to a similar manner to that of Example 199.

The following physical data are those of the dihydrochloride.

mp: 218°–220° C.

IR (Nujol): 1612, 1519, 1495 cm$^{-1}$.

NMR (D$_2$O, δ): 2.58 (3H, s), 3.22 (6H, s), 4.10 (3H, s), 6.83–7.09 (2H, m), 7.85 (1H, d, J=9 Hz), 8.37 (1H, dd, J=8 Hz, 5 Hz), 8.70–8.98 (2H, m), 9.10 (1H, s).

EXAMPLE 202

2-(2-Aminophenyl)-1,5-dimethyl-4-(3-pyridyl)imidazole dihydrochloride was obtained according to a similar manner to that of Example 199.

mp: 285°–286° C.
IR (Nujol): 1587, 1512 cm$^{-1}$.

EXAMPLE 203

To a solution 1-hydroxyimino-1-(3-pyridyl)acetone (0.5 g) in acetic acid (10 ml) was added 2-fluorobenzaldehyde (0.76 g) and ammonium acetate (2.35 g), and refluxed for 30 minutes. Then, the solution was poured into water (75 ml), neutralized with aqueous potassium carbonate, and extracted with ethyl acetate. The extract was dried over magnesium sulfate and concentrated, and the residue was triturated with diisopropyl ether to give 2-(2-fluorophenyl)-1-hydroxy-4-methyl-5-(3-pyridyl)imidazole (0.23 g).

mp: 65°–75° C.
IR (Nujol): 1640, 1572, 1500 cm$^{-1}$.
NMR (DMSO-d$_6$, δ): 2.25 (3H, s), 7.12–7.80 (5H, m), 7.99 (1H, dd, J=8 Hz, 2 Hz, 2 Hz), 8.40–8.92 (2H, m).
MASS (M/Z): 269 (M+).

EXAMPLE 204

The following compounds were obtained according to a similar manner to that of Example 1, 2, 3, 4, 5 or 203.

(1) 1-Hydroxy-2-(4-methoxycarbonylphenyl)-4-methyl-5-(3-pyridyl)imidazole.
mp: 105°–113° C.
IR (Nujol): 1723, 1611 cm$^{-1}$.
NMR (DMSO-d$_6$, δ): 2.25 (3H, s), 3.90 (3H, s), 7.46 (1H, dd, J=8 Hz, 5 Hz), 7.86–8.34 (5H, m), 8.58 (1H, dd, J=5 Hz, 2 Hz), 8.78 (1H, d, J=2 Hz).

(2) 1-Hydroxy-2-(2-mesylaminophenyl)-4-methyl-5-(3-pyridyl)imidazole.
mp: 158°–163° C.
IR (Nujol): 1583, 1495 cm$^{-1}$.
NMR (DMSO-d$_6$, δ): 2.46 (3H, s), 2.97 (3H, s), 7.20–7.95 (5H, m), 8.20 (1H, ddd, J=8 Hz, 2 Hz, 2 Hz), 8.60 (1H, dd, J=5 Hz, 2 Hz), 8.91 (1H, d, J=2 Hz).

(3) 2-(4-Carboxyphenyl)-1-hydroxy-4-methyl-5-(3-pyridyl)imidazole.
mp: 188°–192° C.
IR (Nujol): 1708, 1609 cm$^{-1}$.
NMR (D$_2$O-DCl, δ): 2.60 (3H, s), 8.15–8.26 (4H, m), 8.39 (1H, dd, J=8 Hz, 5 Hz), 8.95–9.20 (2H, m), 9.29 (1H, s).
MASS (M/Z): 295 (M+).

(4) 1-Hydroxy-2-(2-hydroxyphenyl)-4-methyl-5-(3-pyridyl)imidazole.
mp: 201°–202° C.
IR (Nujol): 1629, 1592, 1572, 1486 cm$^{-1}$.
NMR (DMSO-d$_6$, δ): 2.42 (3H, s), 6.80–7.81 (5H, m), 8.19 (1H, ddd, J=8 Hz, 2 Hz, 2 Hz), 8.62 (1H, dd, J=5 Hz, 2 Hz), 8.90 (1H, d, J=2 Hz).

(5) 1-Hydroxy-4-methyl-5-(3-pyridyl)-2-(2-trifluoromethylphenyl)imidazole
mp: 100°–106° C.
IR (Nujol): 1608, 1560, 1482 cm$^{-1}$.
NMR (DMSO-d$_6$, δ): 2.32 (3H, s), 7.35–8.13 (6H, m), 8.58 (1H, dd, J=5 Hz, 2 Hz), 8.80 (1H, d, J=2 Hz).

(6) 1-Hydroxy-5-methyl-2-(2-methylthiophenyl)-4-(3-pyridyl)imidazole
mp: 80°–90° C.
IR (Nujol): 1590, 1550, 1540 cm$^{-1}$.
NMR (DMSO-d$_6$, δ): 2.42 (3H, s), 2.48 (3H, s), 7.20–7.70 (5H, m), 8.15 (1H, ddd, J=8 Hz, 2 Hz, 2 Hz), 8.49 (1H, d, J=5 Hz), 8.96 (1H, d, J=2 Hz).
MASS (M/Z): 297 (M+).

(7) 1-Hydroxy-4-methyl-5-(3-pyridyl)-2-(4-trifluoromethylphenyl)imidazole.
NMR (DMSO-d$_6$, δ): 2.28 (3H, s), 7.50 (1H, dd, J=8 Hz, 5 Hz), 7.70–8.40 (5H, m), 8.56 (1H, m), 8.80 (1H, s).

(8) 2-(4-Acetamidophenyl)-1-hydroxy-4-methyl-5-(3-pyridyl)imidazole.
mp: 156°–161° C.
IR (Nujol): 1690, 1672, 1600, 1530, 1500 cm$^{-1}$.
NMR (DMSO-d$_6$, δ): 2.09 (3H, s), 2.21 (3H, s), 7.45 (1H, dd, J=8 Hz, 5 Hz), 7.50–8.20 (5H, m), 8.52 (1H, dd, J=5 Hz, 2 Hz), 8.75 (1H, d, J=2 Hz), 10.16 (1H, s).

(9) 1-Hydroxy-4-methyl-2-(4-nitrophenyl)-5-(3-pyridyl)imidazole.
mp: 113°–121° C.
IR (Nujol): 1600, 1510 cm$^{-1}$.
NMR (DMSO-d$_6$, δ): 2.38 (3H, s), 7.65 (1H, dd, J=8 Hz, 5 Hz), 8.00–8.55 (5H, m), 8.70 (1H, dd, J=5 Hz, 2 Hz), 8.85 (1H, d, J=2 Hz).

(10) 2-[2-(4-Chlorobenzyloxy)phenyl]-1-hydroxy-4-methyl-5-(3-pyridyl)imidazole.
mp: 201°–203° C.
IR (Nujol): 1620, 1600 cm$^{-1}$.
NMR (DMSO-d$_6$, δ): 2.27 (3H, s), 5.20 (2H, s), 6.86–7.77 (9H, m), 7.93 (1H, d t, J=2, 8 Hz), 8.55 (1H, dd, J=2, 5 Hz), 8.75 (1H, d, J=2 Hz).

(11) 1-Hydroxy-4-methyl-2-(2-methyl-4-acetamidophenyl)-5-(3-pyridyl)imidazole.
mp: 200°–204° C. (dec.).
IR (Nujol): 1670, 1610, 1590, 1530 cm$^{-1}$.

(12) 2-(3-Chloro-4-acetamidophenyl)-1-hydroxy-4-methyl-5-(3-pyridyl)imidazole
mp: 157°–159° C. (dec.).
IR (Nujol): 3250, 1700, 1625, 1565, 1505 cm$^{-1}$.
NMR (DMSO-d$_6$, δ): 2.17 (3H, s), 2.22 (3H, s), 7.47 (1H, dd, J=5, 8 Hz), 7.73–8.17 (3H, m), 8.18 (1H, d, J=2 Hz), 8.55 (1H, dd, J=2, 5 Hz), 8.75 (1H, d, J=2 Hz), 9.57 (1H, s).
MASS (m/e): 342 (M+).

(13) 1-Hydroxy-2-(2-methoxy-4-acetamido-5-nitrophenyl)-4-methyl-5-(3-pyridyl)imidazole.
mp: 182°–183° C.
IR (Nujol): 3470, 3340, 1695, 1620, 1595, 1500 cm$^{-1}$.
NMR (D$_2$O+DCl, δ): 2.43 (3H, s), 2.63 (3H, s), 4.12 (3H, s), 8.17 (1H, s), 8.49 (1H, dd, J=5, 8 Hz), 8.83–9.27 (2H, m), 9.05 (1H, s), 9.32 (1H, d, J=2 Hz).

(14) 1-Hydroxy-2-(2-methoxy-4-chloro-4-nitrophenyl)-4-methyl-5-(3-pyridyl)imidazole.
mp: 171°–172° C. (dec.).
IR (Nujol): 1620, 1600, 1565, 1530, 1520 cm$^{-1}$.
NMR (D$_2$O+DCl, δ): 2.67 (3H, s), 4.20 (3H, s), 7.67 (1H, s), 8.45 (1H, dd, J'5, 8 Hz), 8.87 (1H, s), 8.90–9.23 (2H, m), 9.32 (1H, d, J=2 Hz).

(15) 2-(2-Ethoxyphenyl)-1-hydroxy-4-methyl-5-(3-pyridyl)imidazole.
mp: 101°–103° C.
IR (Nujol): 3350, 1620, 1585, 1250 cm$^{-1}$.
NMR (CDCl$_3$+CD$_3$OD, δ): 1.37 (3H, t, J=7 Hz), 2.24 (3H, s), 4.06 (2H, q, J=7 Hz), 6.8–7.1 (2H, m), 7.2–7.5 (2H, m), 8.01 (1H, dd, J=2 Hz, 7 Hz), 8.17 (1H, dd, J=2 Hz, 7 Hz), 8.48 (1H, dd, J=2 Hz, 5 Hz), 8.61 (1H, d, J=2 Hz).

(16) 1-Hydroxy-2-(2-isopropoxyphenyl)-4-methyl-5-(3-pyridyl)imidazole.
mp: 158°–160° C.

IR (Nujol): 3400, 1600, 1570 cm⁻¹.

NMR (CDCl₃+CD₃OD, δ): 1.41 (6H, d, J=6 Hz), 4.72 (1H, septet, J=6 Hz), 7.0–7.6 (4H, m), 8.1–8.3 (1H, m), 8.5–8.8 (3H, m).

(17) 1-Hydroxy-4-methyl-2-[2-(2-propynyloxy)phenyl]-5-(3-pyridyl)imidazole.

mp: 148°–150° C.

IR (Nujol): 1600, 1580 cm⁻¹.

NMR (CDCl₃+CD₃OD, δ): 2.25 (3H, s), 2.62 (1H, t, J=2 Hz), 4.76 (2H, d, J=2 Hz), 6.8–7.6 (4H, m), 7.8–8.8 (4H, m).

(18) 2-(2-Fluorophenyl)-1-hydroxy-4-methyl-5-(2-pyridyl)imidazole.

mp: 244°–249° C. (dec.).

IR (Nujol): 1590, 1580 cm⁻¹.

NMR (CDCl₃-CD₃OD, δ): 2.55 (3H, s), 6.9–7.5 (4H, m), 7.6–7.8 (2H, m), 7.8–8.2 (1H, m), 8.5–8.7 (1H, m).

(19) 2-(2-Fluorophenyl)-1-hydroxy-4-methyl-5-(4-pyridyl)imidazole.

mp: 249°–251° C.

IR (Nujol): 1600, 1210 cm⁻¹.

NMR (DMSO-d₆, δ): 2.52 (3H, s), 7.2–7.7 (4H, m), 7.82 (2H, dd, J=2 Hz, 5 Hz), 8.52 (2H, dd, J=2 Hz, 5 Hz).

(20) 2-(2-Methoxy-4-chloro-5-nitrophenyl)-4-methyl-5-(3-pyridyl)imidazole.

mp: 234°–6° C. (dec.).

IR (Nujol): 1600, 1570, 1510 cm⁻¹.

(21) 2-[2-(4-Chlorobenzyloxy)phenyl]-4-methyl-5-(3-pyridyl)imidazole.

mp: 106°–108° C.

IR (Nujol): 3410, 1600, 1585, 1550, 1530 cm⁻¹.

(22) 4-Methyl-2-(2-methyl-4-acetamidophenyl)-5-(3-pyridyl)imidazole.

mp: 285°–287° C.

IR (Nujol): 3220, 1675, 1620, 1550, 1500 cm⁻¹.

(23) 2-(2-Methoxy-4-acetamido-5-nitrophenyl)-4-methyl-5-(3-pyridyl)imidazole.

mp: 220°–221° C.

IR (Nujol): 3360, 3330, 1695, 1620, 1590, 1535 cm⁻¹.

(24) 2-(2-Ethoxyphenyl)-4-methyl-5-(3-pyridyl)imidazole.

mp: 166°–168° C.

IR (Nujol): 3230, 1590, 1555, 1520 cm⁻¹.

(25) 2-(2-Isopropoxyphenyl)-4-methyl-5-(3-pyridyl)imidazole.

mp: 168°–169° C.

IR (Nujol): 3420, 1590, 1560, 1235 cm⁻¹.

(26) 4-Methyl-2-[2-(2-propynyloxy)phenyl]-5-(3-pyridyl)imidazole.

mp: 167°–169° C.

IR (Nujol): 3320, 1590, 1560, 1510 cm⁻¹.

(27) 2-(2-Fluorophenyl)-4-methyl-5-(2-pyridyl)imidazole.

mp: 128°–130° C.

IR (Nujol): 1600, 1590, 1490 cm⁻¹.

(28) 2-(2-Fluorophenyl)-4-methyl-5-(4-pyridyl)imidazole.

mp: 192°–193° C.

IR (Nujol): 1595, 1570 cm⁻¹.

(29) 2-(2-Fluorophenyl)-4-(3-pyridyl)imidazole.

mp: 144°–145° C.

IR (Nujol): 1605, 1586, 1556, 1485 cm⁻¹.

(30) 2-(2-Hydroxyphenyl)-4-methyl-5-(3-pyridyl)imidazole.

mp: 265°–266° C.

IR (Nujol): 1600, 1575, 1494 cm⁻¹.

(31) 2-(2-Mesylaminophenyl)-4-methyl-5-(3-pyridyl)imidazole.

mp: 245°–246° C.

IR (Nujol): 1600, 1577, 1497 cm⁻¹.

(32) 2-(4-Methoxycarbonylphenyl)-4-methyl-5-(3-pyridyl)imidazole.

mp: 160°–168° C.

IR (Nujol): 1733, 1616, 1600, 1569 cm⁻¹.

(33) 2-(4-Carboxyphenyl)-4-methyl-5-(3-pyridyl)imidazole.

mp: >280° C.

IR (Nujol): 1675, 1611, 1568 cm⁻¹.

(34) 4-Methyl-2-(2-methylthiophenyl)-5-(3-pyridyl)imidazole.

mp: 200°–201° C.

IR (Nujol): 1600, 1576, 1489 cm⁻¹.

(35) 4-Methyl-5-(3-pyridyl)-2-(2-trifluoromethylphenyl)imidazole.

mp: 131°–132° C.

IR (Nujol): 1609, 1575, 1500 cm⁻¹.

(36) 2-(4-Acetamido-3-chlorophenyl)-4-methyl-5-(3-pyridyl)imidazole.

mp: 262°–264° C.

IR (Nujol): 3210, 1665, 1580, 1540 cm⁻¹.

(37) 2-(2-Methoxy-4-chloro-5-aminophenyl)-4-methyl-5-(3-pyridyl)imidazole mp: 173°–175° C.

IR (Nujol): 3300, 3200, 1630, 1580, 1565, 1520 cm⁻¹.

(38) 2-(2-Methoxy-4-chloro-5-acetamidophenyl)-4-methyl-5-(3-pyridyl)imidazole mp: 274°–276° C. (dec.).

IR (Nujol): 3250, 1660, 1600, 1590, 1570, 1535 cm⁻¹,

(39) 1-Hydroxy-4-methyl-5-(3-pyridyl)-2-(2-tosylaminophenyl)imidazole.

mp: 103°–113° C. IR (Nujol): 3520, 1658, 1590 cm⁻¹.

NMR (DMSO-d₆, δ): 2.32 (6H, s), 7.10–7.78 (9H, m), 8.24 (1H, ddd, J=8 Hz, 2 Hz, 2 Hz), 8.65 (1H, dd, J=5 Hz, 2 Hz), 8.95 (1H, d, J=2 Hz).

(40) 4-Methyl-5-(3-pyridyl)-2-(2-tosylaminophenyl)imidazole.

mp: 282°–284° C.

IR (Nujol): 3530, 1665, 1599, 1570, 1495 cm⁻¹.

(41) 4-Methyl-2-[2-(3-nitrobenzoylamino)phenyl]-5-(3-pyridyl)imidazole.

mp: 257°–259° C.

IR (Nujol): 1675, 1625, 1600, 1525, 1490 cm⁻¹.

(42) 4-Methyl-2-[2-(3-methylthioureido)phenyl]-5-(3-pyridyl)imidazole.

mp: 192°–193° C.

IR (Nujol): 1570, 1520, 1490 cm⁻¹.

(43) 2-[2-(3-benzoylthioureido)phenyl]-4-methyl-5-(3-pyridyl)imidazole mp: 159°–161° C.

IR (Nujol): 3405, 3180, 2070, 1680, 1615, 1582, 1510 cm⁻¹.

(44) 2-(2-methoxycarbonylaminophenyl)-4-methyl-5-(3-pyridyl)imidazole.

mp: 221°–223° C.

IR (Nujol): 1732, 1599, 1570, 1538, 1490 cm⁻¹.

EXAMPLE 205

A mixture of 1-hydroxy-2-(2-methoxy-4-chloro-5-nitrophenyl)-4-methyl-5-(3-pyridyl)imidazole (9.7 g) and triethyl phosphite (8.9 g) in N,N-dimethylformamide (100 ml) was stirred at 80°–90° C. for one hour. The reaction mixture was poured into water and the resultant mixture was stirred at ambient temperature for one hour. The precipitate was collected by filtration and washed with water and ethyl acetate and dried to give 2-(2-methoxy-4-chloro-5-nitrophenyl)-4-methyl-5-(3-pyridyl)imidazole (7.6 g).

mp: 234°–236° C. (dec.).

IR (Nujol): 1600, 1570, 1510 cm$^{-1}$.

NMR (D$_2$O+DCl, δ): 2.68 (3H, s), 4.22 (3H, s), 7.63 (1H, s), 8.38 (1H, dd, J=5, 8 Hz), 8.78 (1H, s), 8.92–9.17 (2H, m), 9.28 (1H, d, J=2 Hz).

MASS (m/e): 344 (M+).

EXAMPLE 206

The following compounds were obtained according to a similar manner to that of Example 120, 121, 122, 123, 124 or 205.

(1) 2-[2-(4-Chlorobenzyloxy)phenyl]-4-methyl-5-(3-pyridyl)imidazole.

mp: 106°–108° C. (recrystallized from a mixture of ethyl acetate and diethyl ether).

IR (Nujol): 3410, 1600, 1585, 1550, 1530 cm$^{-1}$.

NMR (DMSO-d$_6$, δ): 2.52 (3H, s), 5.36 (2H, s), 6.85–7.63 (9H, m), 8.03 (1H, dd, J=2, 8 Hz), 8.40 (1H, dd, J=2, 5 Hz), 8.90 (1H, d, J=2 Hz), 11.70 (1H, br s).

MASS (m/e): 375 (M+).

(2) 4-Methyl-2-(2-methyl-4-acetamidophenyl)-5-(3-pyridyl)imidazole.

mp: 285°–287° C. (recrystallized from a mixture of methanol and ethyl acetate).

IR (Nujol): 3220, 1675, 1620, 1550, 1500 cm$^{-1}$.

NMR (DMSO-d$_6$, δ): 2.06 (3H, s), 2.47 (3H, s), 2.60 (3H, s), 7.36 (1H, dd, J=5, 8 Hz), 7.43–7.60 (3H, m), 8.00 (1H, d t, J=2, 8 Hz), 8.37 (1H, dd, J=2, 5 Hz), 8.86 (1H, d, J=2 Hz), 9.66 (1H, s), 12.10 (1H, br s).

MASS (m/e): 306 (M+).

(3) 2-(2-Methoxy-4-acetamido-5-nitrophenyl)-4-methyl-5-(3-pyridyl)imidazole.

mp: 220°–221° C.

IR (Nujol): 3360, 3330, 1695, 1620, 1590, 1535 cm$^{-1}$.

NMR (DMSO-d$_6$, δ): 2.20 (3H, s), 2.53 (3H, s), 4.11 (3H, s), 7.47 (1H, dd, J=5, 8 Hz), 7.90 (1H, s), 8.12 (1H, d t, J=2, 8 Hz), 8.48 (1H, dd, J=2, 5 Hz), 8.77 (1H, s), 8.95 (1H, d, J=2 Hz), 10.42 (1H, br s), 11.70 (1H, m).

(4) 2-(2-Ethoxyphenyl)-4-methyl-5-(3-pyridyl)imidazole.

mp: 166°–168° C.

IR (Nujol): 3230, 1590, 1555, 1520 cm$^{-1}$.

NMR (CDCl$_3$+CD$_3$OD, δ): 1.56 (3H, t, J=7 Hz), 2.47 (3H, s), 4.24 (2H, q, J=7 Hz), 6.9–7.6 (4H, m), 7.9–8.5 (3H, m), 8.85 (1H, J=2 Hz).

MASS (m/e): 279 (M+).

(5) 2-(2-Isopropoxyphenyl)-4-methyl-5-(3-pyridyl)imidazole.

mp: 168°–169° C.

IR (Nujol): 3420, 1590, 1560, 1235 cm$^{-1}$.

NMR (CD$_3$OD+CDCl$_3$, δ): 1.35 (6H, d, J=6.5 Hz), 2.53 (3H, s), 4.80 (1H, sep, J=6.5 Hz), 6.9–7.6 (4H, m), 7.9–8.5 (3H, m), 8.84 (1H, d, J=3 Hz).

MASS (m/e): 293 (M+).

(6) 4-Methyl-2-[2-(2-propynyloxy)phenyl]-5-(3-pyridyl)imidazole.

mp: 167°–169° C.

IR (Nujol): 3320, 1590, 1560, 1510 cm$^{-1}$. NMR (CDCl$_3$+CD$_3$OD, δ): 2.51 (3H, s), 2.77 (1H, t, J=2 Hz), 4.86 (2H, d, J=2 Hz), 6.9–7.5 (4H, m), 7.9–8.5 (3H, m), 8.83 (1H, d, J=2 Hz).

MASS (m/e): 289 (M+).

(7) 2-(2-Fluorophenyl)-4-methyl-5-(2-pyridyl)imidazole.

mp: 128°–130° C.

IR (Nujol): 1600, 1590, 1490 cm$^{-1}$.

NMR (CDCl$_3$+CD$_3$OD, δ): 2.61 (3H, s), 5.40 (1H, br s), 6.9–7.4 (4H, m), 7.6–7.8 (2H, m), 8.0–8.4 (1H, m), 8.4–8.6 (1H, m).

MASS (m/e): 253 (M+).

(8) 2-(2-Fluorophenyl)-4-methyl-5-(4-pyridyl)imidazole.

mp: 192°–193° C.

IR (Nujol): 1595, 1570 cm$^{-1}$.

NMR (CDCl$_3$+CD$_3$OD, δ): 2.52 (3H, s), 6.9–7.4 (3H, m), 7.65 (2H, dd, J=2 Hz, 5 Hz), 8.53 (2H, dd, J=2 Hz, 5 Hz), 8.0–8.4 (1H, m).

MASS (m/e): 253 (M+).

(9) 2-(2-Fluorophenyl)-4-(3-pyridyl)imidazole.

mp: 144°–145° C.

IR (Nujol): 1605, 1586, 1556, 1485 cm$^{-1}$.

NMR (DMSO-d$_6$, δ): 7.25–7.68 (4H, m), 8.00–8.20 (2H, m), 8.28 (1H, ddd, J=8 Hz, 2 Hz, 2 Hz), 8.48 (1H, dd, J=5 Hz, 2 Hz), 9.22 (1H, d, J=2 Hz).

MASS (M/Z): 239 (M+).

(10) 2-(2-Hydroxyphenyl)-4-methyl-5-(3-pyridyl)imidazole.

mp: 265°–266° C.

IR (Nujol): 1600, 1575, 1494 cm$^{-1}$.

NMR (DMSO-d$_6$, δ): 2.52 (3H, s), 6.75–7.03 (2H, m), 7.20 (1H, dd, J=8 Hz, 2 Hz), 7.44 (1H, dd, J=8 Hz, 5 Hz), 7.70–8.11 (2H, m), 8.46 (1H, dd, J=5 Hz, 2 Hz), 8.85 (1H, d, J=2 Hz).

MASS (M/Z): 251 (M+).

(11) 2-(2-Mesyl aminophenyl)-4-methyl-5-(3-pyridyl)imidazole mp: 245°–246° C.

IR (Nujol): 1600, 1577, 1497 cm$^{-1}$.

NMR (DMSO-d$_6$, δ): 2.54 (3H, s), 3.11 (3H, s), 7.08–7.68 (4H, m), 7.81–8.11 (2H, m), 8.47 (1H, dd, J=3 Hz, 2 Hz), 8.93 (1H, d, J=2 Hz), 12.83 (1H, br s).

(12) 2-(4-Methoxycarbonylphenyl)-4-methyl-5-(3-pyridyl)imidazole.

mp: 160°–168° C.

IR (Nujol): 1733, 1616, 1600, 1569 cm$^{-1}$.

NMR (DMSO-d$_6$, δ): 2.56 (3H, s), 3.90 (3H, s), 7.42 (1H, dd, J=8 Hz, 5 Hz), 7.88–8.30 (5H, m), 8.43 (1H, dd, J=5 Hz, 2 Hz), 8.92 (1H, d, J=2 Hz).

MASS (M/Z): 293 (M+).

(13) 2-(4-Carboxyphenyl)-4-methyl-5-(3-pyridyl)imidazole.

mp: >280° C.

IR (Nujol): 1675, 1611, 1568 cm$^{-1}$.

NMR (DMSO-d$_6$, δ): 2.69 (3H, s), 7.61 (1H, dd, J=8 Hz, 5 Hz), 8.05–8.40 (5H, m), 8.61 (1H, d, J=5 Hz), 9.09 (1H, s).

MASS (M/Z): 279 (M+).

(14) 4-Methyl-2-(2-methylthiophenyl)-5-(3-pyridyl)imidazole.

mp: 200°–201° C.

IR (Nujol): 1600, 1576, 1489 cm$^{-1}$.

NMR (DMSO-d$_6$, δ): 2.40 (3H, s), 2.50 (3H, s), 7.12–7.76 (5H, m), 8.09 (1H, ddd, J=8 Hz, 2 Hz, 2 Hz), 8.42 (1H, dd, J=5 Hz, 2 Hz), 8.96 (1H, d, J=2 Hz).

MASS (M/Z): 281 (M+).

(15) 4-Methyl-5-(3-pyridyl)-2-(2-trifluoromethylphenyl)imidazole.

mp: 131°–132° C.

IR (Nujol): 1609, 1575, 1500 cm$^{-1}$.

NMR (DMSO-d$_6$, δ): 2.52 (3H, s), 7.45 (1H, dd, J=8 Hz, 5 Hz), 7.60–8.00 (4H, m), 8.10 (1H, ddd, J=8 Hz, 2 Hz, 2 Hz), 8.45 (1H, dd, J=5 Hz, 2Hz), 8.95 (1H, d, J=2 Hz).

MASS (M/Z): 303 (M+).

(16) 2-(4-Acetamido-3-chlorophenyl)-4-methyl-5-(3-pyridyl)imidazole. mp: 262°-264° C.

IR (Nujol): 3210, 1665, 1580, 1540 cm$^{-1}$.

NMR (DMSO-d$_6$, δ): 2.16 (3H, s), 2.52 (3H, s), 7.40 (1H, dd, J=5, 8 Hz), 7.87 (2H, s), 8.84 (2H, br s), 8.43 (1H, d, J=5 Hz), 8.91 (1H, br s), 9.50 (1H, s), 12.53 (1H, br s).

(17) 4-Methyl-5-(3-pyridyl)-2-(2-tosylaminophenyl)imidazole.

mp: 282°-284° C.

IR (Nujol): 3530, 1665, 1599, 1570, 1495 cm$^{-1}$.

NMR (DMSO-d$_6$, δ): 2.24 (3H, s), 2.50 (3H, s), 6.95-7.91 (9H, m), 8.04 (1H, d, J=8 Hz), 8.48 (1H, d, J=5 Hz), 8.95 (1H, s), 13.00 (1H, br s).

(18) 2-(2-Methoxy-4-chloro-5-aminophenyl)-4-methyl-5-(3-pyridyl)imidazole.

mp: 173°-175° C.

IR (Nujol): 3300, 3200, 1630, 1580, 1565, 1520 cm$^{-1}$.

(19) 2-(2-Methoxy-4-chloro-5-acetamidophenyl)-4-methyl-5-(3-pyridyl)imidazole.

mp: 274°-276° C. (dec.).

IR (Nujol): 3250, 1660, 1600, 1590, 1570, 1535 cm$^{-1}$.

(20) 4-Methyl-2-[2-(3-nitrobenzoylamino)phenyl]-5-(3-pyridyl)imidazole.

mp: 257°-259° C.

IR (Nujol): 1675, 1625, 1600, 1525, 1490 cm$^{-1}$.

(21) 4-Methyl-2-[2-(3-methylthioureido)phenyl]-5-(3-pyridyl)imidazole.

mp: 192°-193° C.

IR (Nujol): 1570, 1520, 1490 cm$^{-1}$.

(22) 2-[2-(3-benzoylthioureido)phenyl]-4-methyl-5-(3-pyridyl)imidazole.

mp: 159°-161° C.

IR (Nujol): 3405, 3180, 2070, 1680, 1615, 1582, 1510 cm$^{-1}$.

(23) 2-(2-methoxycarbonylaminophenyl)-4-methyl-5-(3-pyridyl)imidazole.

mp: 221°-223° C.

IR (Nujol): 1732, 1599, 1570, 1538, 1490 cm$^{-1}$.

EXAMPLE 207

A mixture of 2-(2-methoxy-4-chloro-5-nitrophenyl)-4-methyl-5-(3-pyridyl)imidazole (6.4 g), 1N-hydrochloric acid (37 ml) and 10% palladium on carbon (3 g) in methanol (100 ml) was subjected to catalytic reduction at ambient temperature under atmospheric pressure of hydrogen gas for 3 hours. The reaction mixture was filtered and the filtrate was evaporated in vacuo. The residue was dissolved in water and the solution was adjusted to pH 8.0 with 20% aqueous potassium carbonate. The resultant mixture was extracted with ethyl acetate and extract was dried over magnesium sulfate. The solvent was evaporated in vacuo and the residue was subjected to column chromatography on silica gel and eluted with a mixture of chloroform and methanol (96:4 V/V). The fractions containing object compound were evaporated in vacuo and the residue was recrystallized from a mixture of ethyl acetate and diisopropyl ether to give 2-(2-methoxy-4-chloro-5-aminophenyl)-4-methyl-5-(3-pyridyl)imidazole (2.1 g).

mp: 173°-175° C.

IR (Nujol): 3300, 3200, 1630, 1580, 1565, 1520 cm$^{-1}$.

NMR (DMSO-d$_6$, δ): 2.55 (3H, s), 3.90 (3H, s), 5.03 (2H, s), 7.09 (1H, s), 7.45 (1H, dd, J=5, 8 Hz), 7.70 (1H, s), 8.08 (1H, dt, J=2, 8 Hz), 8.45 (1H, dd, J=5 Hz), 8.97 (1H, d, J=2 Hz), 11.50 (1H, br s).

MASS (m/e): 314 (M+).

EXAMPLE 208

A solution of 2-(2-methoxy-4-chloro-5-aminophenyl)-4-methyl-5-(3-pyridyl)imidazole (1.0 g) and acetic anhydride (2 ml) in a mixture of ethyl acetate (20 ml) and tetrahydrofuran (10 ml) was refluxed for 2 hours. The reaction mixture was cooled with ice-water and the crystalline residue was collected by filtration to give 2-(2-methoxy-4-chloro-5-acetamidophenyl)-4-methyl-5-(3-pyridyl)imidazole (0.7 g).

mp: 274°-276° C. (dec.).

IR (Nujol): 3250, 1660, 1600, 1590, 1570, 1535 cm$^{-1}$.

NMR (D$_2$O+DCl, δ): 2.30 (3H, s), 2.65 (3H, s), 4.06 (3H, s), 7.45 (1H, s), 8.06 (1H, s), 5.70 (1H, dd, J=5, 7 Hz), 8.83-9.06 (2H, m), 9.21 (1H, d, J=2 Hz).

MASS (m/e): 356 (M+).

EXAMPLE 209

The following compounds were obtained according to a similar manner to that of Example 195 or 208.

(1) 2-(4-Acetamido-5-chloro-2-methoxyphenyl)-5-methyl-4-(3-pyridyl)imidazole.

mp: 239°-240° C.

IR (Nujol): 3400, 1680, 1590, 1520, 1490 cm$^{-1}$.

(2) 2-(4-Acetamido-2-methoxyphenyl)-5-methyl-4-(3-pyridyl)imidazole.

mp: 215°-218° C.

IR (Nujol): 1675, 1600 cm$^{-1}$.

(3) 4-Methyl-2-(2-methyl-4-acetamidophenyl)--(3-pyridyl)imidazole.

mp: 285°-287° C.

IR (Nujol): 3220, 1675, 1620, 1550, 1500 cm$^{-1}$.

(4) 2-(2-Methoxy-4-acetamido-5-nitrophenyl)-4-methyl-5-(3-pyridyl)imidazole.

mp: 220°-221° C.

IR (Nujol): 3360, 3330, 1695, 1620, 1590, 1535 cm$^{-1}$.

(5) 2-(4-Acetamido-3-chlorophenyl)-4-methyl-5-(3-pyridyl)imidazole.

mp: 262°-264° C.

IR (Nujol): 3210, 1665, 1580, 1540 cm$^{-1}$.

EXAMPLE 210

2-(2-Methoxyphenyl)-4-methyl-5-(3-pyridyl)imidazole dihydrochloride was obtained according to a similar manner to that of Example 199.

mp: 228°-230° C.

IR (Nujol): 1630, 1580 cm$^{-1}$.

NMR (DMSO-d$_6$, δ): 2.60 (3H, s), 4.01 (3H, s), 8.4-7.0 (5H, m), 9.0-8.6 (2H, m), 9.24 (1H, d, J=2 Hz).

EXAMPLE 211

To a solution of 2-(2-Aminophenyl)-4-methyl-5-(3-pyridyl)imidazole (0.8 g) and triethylamine (0.49 ml) in methylene chloride (10 ml) was added a solution of 3-nitrobenzoyl chloride (0.65 g) in methylene chloride (5 ml) under ice cooling. The reaction solution was stirred for one hour. The reaction mixture was poured into water (50 ml), extracted with a mixture of chloroform and methanol, and dried over magnesium sulfate. The solvent was distilled off, and a residue was triturated with ethyl acetate to give 4-methyl-2-[2-(3-nitobenzoylamino)phenyl]-5-(3-pyridyl)imidazole (0.95 g).

mp: 257°-259° C.

IR (Nujol): 1675, 1625, 1600, 1525, 1490 cm$^{-1}$.

NMR (DMSO-d$_6$, δ): 2.51 (3H, s), 7.10-8.20 (6H, m), 8.31-8.95 (6H, m).

EXAMPLE 212

To a solution of 2-(2-aminophenyl)-4-methyl-5-(3-pyridyl)imidazole (0.8 g) in tetrahydrofuran (10 ml) was added methyl isothiocyanate (0.33 ml) at ambient temperature. The reaction mixture was stirred at ambient temperature for one hour, and refluxed for 20 hours. The resulting precipitate was collected by filtration, and washed with tetrahydrofuran and diethyl ether to give 4-methyl-2-[2-(3-methylthioureido)phenyl]-5-(3-pyridyl)imidazole (0.71 g).

mp: 192°–193° C.

IR (Nujol): 1570, 1520, 1490 cm$^{-1}$.

NMR (DMSO-d$_6$, δ): 2.50 (3H, s), 2.95 (3H, d, J=5 Hz), 6.98–7.52 (3H, m), 7.68–8.60 (5H, m), 8.99 (1H, s), 14.30 (1H, s), 15.07 (1H, s).

EXAMPLE 213

To a solution of 2-(2-aminophenyl)-4-methyl-5-(3-pyridyl)imidazole (1.60 g) in methylene chloride (20 ml) was added a solution of benzoyl isothiocyanate (1.04 g) in methylene chloride (5 ml) at ambient temperature. The reaction mixture was stirred at ambient temperature for one hour. The resulting precipitate was collected by filtration. The precipitate was washed with methylene chloride, ethanol, and diethyl ether to give 2-[2-(3-benzoylthioureiedo)phenyl]-4-methyl-5-(3-pyridyl)imidazole (1.95 g).

mp: 159°–161° C.

IR (Nujol): 3405, 3180, 2070, 1680, 1615, 1582, 1510, cm$^{-1}$.

NMR (DMSO-d$_6$, δ): 2.50 (3H, s), 7.00–8.49 (12H, m), 8.97 (1H, s), 11.38 (1H, s).

EXAMPLE 214

To a suspension of 2-(2-Aminophenyl)-4-methyl-5-(3-pyridyl)imidazole (0.80 g) and triethylamine (0.49 ml) in methylene chloride (10 ml) was added methyl chloroformate (0.27 ml) under ice-cooling.

The reaction mixture was stirred at ambient temperature for one hour, and the resulting precipitate was collected by filtration and triturated by water and ethyl acetate. The residue was recrystallized from ethanol to give 2-(2-methoxycarbonylaminophenyl)-4-methyl-5-(3-pyridyl)imidazole (0.50 g).

mp: 221°–223° C.

IR (Nujol): 1732, 1599, 1570, 1538, 1490 cm$^{-1}$.

NMR (DMSO-d$_6$, δ): 2.50 (3H, s), 3.73 (3H, s), 7.00–7.55 (3H, m), 7.80–8.11 (2H, m), 8.20–8.54 (2H, m), 8.94 (1H, s).

What we claim is:

1. A compound of the formula:

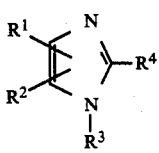

wherein R$^1$ is pyridyl,

R$^2$ is hydrogen, lower alkyl or hydroxy(lower)alkyl,

R$^3$ is hydrogen, hydroxy or lower alkyl, and

R$^4$ is phenyl substituted with hydroxy; with halo(lower)alkyl; with nitro; with amino; with lower alkanoylamino; with nitro-substituted or unsubstituted benzoylamino; with ureido; with lower alkylureido; with thioureido; with lower alkylthioureido; with benzoylthioureido; with lower alkylsulfonylamino; with tosylamino; with lower alkoxycarbonylamino; with halogen-substituted or unsubstituted phenyl(lower)alkoxy; with lower alkynyloxy; with carboxy; with lower alkoxycarbonyl; with lower alkoxy and lower alkylsulfinyl; with lower alkoxy and lower alkylsulfonyl; with lower alkoxy and hydroxy; with lower alkoxy and halogen-substituted or unsubstituted phenyl(lower)alkoxy; with lower alkoxy and nitro; with lower alkoxy and amino; with lower alkoxy and lower alkanoylamino; with lower alkoxy and (mono- or di(lower)alkyl)amino; with halogen and lower alkanoylamino; with lower alkyl and lower alkanoylamino; with lower alkoxy, halogen and hydroxy; with lower alkoxy, halogen and nitro; with lower alkoxy, halogen and amino; with lower alkanoylamino, lower alkoxy and halogen; with lower alkoxy, halogen and lower alkylamino; with lower alkoxy, halogen and N-lower alkanoyl-N-lower alkylamino; or with lower alkoxy, nitro and lower alkanoylamino; and a pharmaceutically acceptable salt thereof.

2. A cardiotonic pharmaceutical composition comprising a cardiotonic effective amount of a compound of claim 1, as an active ingredient, in association with a pharmaceutically acceptable, substantially nontoxic carrier or excipient.

3. An anti-platelet aggregation pharmaceutical composition comprising an anti-platelet aggregation effective amount of a compound of claim 1, as an active ingredient, in association with a pharmaceutically acceptable, substantially nontoxic carrier or excipient.

4. An anti-inflammatory pharmaceutical composition comprising an anti-inflammatory effective amount of a compound of claim 1, as an active ingredient, in association with a pharmaceutically acceptable, substantially nontoxic carrier or excipient.

5. A compound of claim 1, wherein R$^4$ is phenyl substituted with lower alkanoylamino.

6. A compound of claim 5, which is 2-(2-acetamidophenyl)-4-methyl-5-(3-pyridyl)imidazole.

7. A compound of claim 1, wherein R$^4$ is phenyl substituted with lower alkanoylamino, lower alkoxy and halogen.

8. A compound of claim 7, which is 2-(4-acetamido-5-chloro-2-methoxyphenyl)-5-methyl-4-(3-pyridyl)imidazole.

9. A method for therapeutic treatment of heart disease, thrombosis and inflammation which comprises administering a compound of claim 1 to human beings or animals.

* * * * *